(12) United States Patent
Bonini et al.

(10) Patent No.: US 6,221,660 B1
(45) Date of Patent: Apr. 24, 2001

(54) DNA ENCODING SNORF25 RECEPTOR

(75) Inventors: James A. Bonini, Oakland; Beth E. Borowsky, Montclair; Nika Adham, Ridgewood; Noel Boyle, Cliffside Park; Thelma O. Thompson, Passaic Park, all of NJ (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/387,699

(22) Filed: Aug. 13, 1999

Related U.S. Application Data

(63) Continuation-in-part of application No. 09/255,376, filed on Feb. 22, 1999.

(51) Int. Cl.[7] .................................. C12N 5/18; C12N 5/22
(52) U.S. Cl. ..................... 435/348; 530/350; 536/23.5; 435/357; 435/361; 435/365; 435/369
(58) Field of Search .................. 530/350; 536/23.5; 435/320.1, 252.3

(56) References Cited

FOREIGN PATENT DOCUMENTS

| 9325677 | 12/1993 | (WO) . |
| 0022131 | 4/2000 | (WO) . |
| 0031258 | 6/2000 | (WO) . |

OTHER PUBLICATIONS

GenEMBL Database Accession No. AC002537, published Apr. 18, 1999.
GenEMBL Database Accession No. AF017283, published Sep. 18, 1997.

Pearce, A., Human DNA sequence from clone 2013 on chromosome Xq25–26 contains a gene for brain mitochrondrial carrier protein–1 (BMCP1), ESTs, STSs, GSSs, and a CpG island, complete sequence. GenEMbl, Accession No. AL035423, Nov. 1999.*

* cited by examiner

*Primary Examiner*—Lorraine Spector
*Assistant Examiner*—Eileen B. O'Hara
(74) *Attorney, Agent, or Firm*—John P. White; Cooper & Dunham LLP

(57) ABSTRACT

This invention provides isolated nucleic acids encoding mammalian SNORF25 receptors, purified mammalian SNORF25 receptors, vectors comprising nucleic acid encoding mammalian SNORF25 receptors, cells comprising such vectors, antibodies directed to mammalian SNORF25 receptors, nucleic acid probes useful for detecting nucleic acid encoding mammalian SNORF25 receptors, antisense oligonucleotides complementary to unique sequences of nucleic acid encoding mammalian SNORF25 receptors, transgenic, nonhuman animals which express DNA encoding normal or mutant mammalian SNORF25 receptors, methods of isolating mammalian SNORF25 receptors, methods of treating an abnormality that is linked to the activity of the mammalian SNORF25 receptors, as well as methods of determining binding of compounds to mammalian SNORF25 receptors, methods of identifying agonists and antagonists of SNORF25 receptors, and agonists and antagonists so identified.

21 Claims, 14 Drawing Sheets

FIGURE 1A

```
1   TGAGAATTTCAGCTGGAGAGATAGCATGCCCTGGTAAGTGAAGTCCTGCCACTTCGAGAC    60
61  ATGGAATCATCTTTCTCATTTGGAGTGATCCTTGCCTGTGTCCTGGCCTCCCTCATCATTGCT  120
121 ACTAACACACTAGTGGCTGTGTGGCTGTGTGTGATCCACAAGAATGATGGTGTCAGT   180
181 CTCTGCTTCACCTTGAATCTGGCTGTGTGGCTGACACCTTGATTGGTGGCCATCTCTGGC   240
241 CTACTCACAGACCAGCTCTCCGGCCCACACAGAAGACCCTGTGCAGCCTG   300
301 CGGATGGCATTTGTCACTTCCTCCCCAGCTGCCTCTGTCCTCACGGTCATGCTGATCACC   360
361 TTTGACAGGTACCTTGCCATCAAGCAGCCCTTCCGCTACTTGAAGATCATGAGTGGGTTC   420
421 GTGGCCGGGCCTGCATTGCCGGGTGTGGTTAGTGTCTTACCTCATTGGCTTCCTCCCA   480
481 CTCGGAATCCCCATGTTCCAGCAGACTGCCAGTGCCTACAAAGGGCAGCTTCTTGCTGTA   540
541 TTTCACCCTCACTTCGTGCTGACCCTCTCCTGCGTTGGCTTCTTCCCAGCCATGCTCCTC   600
```

FIGURE 1B

```
601   TTTGTCTTCTTCTACTGGACATGCTCAAGATGCCTCCATGCACAGCCAGCAGATTCGA    660
661   AAGATGGAACATGCAGGAGCCATGGCTGGAGGTTATCGATCCCCAGGACTCCCAGCGAC    720
721   TTCAAAGCTCTCCGTACTGTGTCTGTTCTGTTCTCATTGGGAGCTTTGCTCTATCCTGGA    780
781   TTCCTTATCACTGGCATTGTGCAGGTGGCCTGCCAGGAGTGTCACCTCTACCTAGTGCTG    840
841   GAACGGTACCTGTGGCTGCTCGGCGTGGGCAACTCCCTGCTCAACCCACTCATTCTATGCC    900
901   TATTGGCAGAAGGAGGTGCGACTGCAGCTCTACCACATGGCCCTAGGAGTGAAGAAGGTG    960
961   CTCACCTCATTCCTCCTCTTTCTCTCGGCCCAGGAATTGTGGCCCAGAGAGGCCCAGGAA   1020
1021  AGTTCCTGTCACATGTCACTATCTCCAGCTCAGAGTTTGATGGCTAAGACGGTAAGGGC   1080
1081  AGAGAAGTTTCAAAGTGCCTTTCTCCCTCCCCACTCTGGAGCCCCCAACTAG          1129
```

```
  1  TCAAGACCCAGCATGCCCTTATAAGTGGGAGTCCTGCTACCTCGAACCATGGAGTCATCT   60
 61  TTCTCATTGGAGTGATCCTTGCTGTCCTGACCATCCTTATCATTGCTGTGTTAATGCGCTG  120
121  GTGGTTGTGGCTATGCTGCTATCAATCTACAAGAATGATGGTGTTGGCCTTTGCTTCACC  180
181  TTAAATCTGGCCGTGGCTGATACCTTGATTGGCGTGGCTATTCTGGGCTAGTTACAGAC  240
241  CAGCTCTCCAGCTCTGCTCAGCACACAGAAGACCTTGTGTAGCCTTCGGATGGCATTC    300
301  GTCACTTCTTCTGCAGCCGCCCTCTGTCCTCACGGTCATGCTCGATTGCCTTTGACAGGTAC  360
361  CTGGCCATTAAGCAGCCCCCTCCCCGTTACTTCCAGATCATGAATGGGGCTTGTAGCCGGAGGA  420
421  TGCATTGCAGGGCTGTGGTTGATATCTTACCTTATCGGCTTCCTCCCACTTGGAGTCTCC  480
481  ATATTCCAGCAGACCACCTACCATGGGCCCTGCACCCTTCTTTGCTGTGTTTCACCCAAGG  540
541  TTTGTGCTGACCCCTCTCCTGCTTCTTCCCAGCTGTGCTCCTCTTTGTCTTCTTC      600
601  TACTGTGACATGCTCAAGATTGCCTCTGTGCACAGCCAGCACATCCGGAAGATGGAACAT  660
```

FIGURE 3B

```
661   GCAGGAGCCATGGTTGCCGGGCCCCACGGCCTGTCAATGACTTCAAGGCTGTC   720
721   CGGACTGTATCTGTCCCTTATTGGGAGCTTCACCCTGTCCTGGTCTCCGTTTCTCATCACT   780
781   AGCATTGTGCAGGTGGCCCTGCCACAAATGCTGCCTCTACCAAGTGCTGGAAAAATACCTC   840
841   TGGCTCCCTTGAGTTGGCAACTCCCCTGCTCAACCCCACTCATCTATGCCTATTGGCAGAGG   900
901   GAGGTTCGGGCCAGCAGCTCTGCCACATGGCCCTGGGGTGAAGAAGTTCTTTACTTCAATC   960
961   TTCCTCCTCTCTCGGCCCAGGAATCGTGGTCCACAGAGACCCGAGAAAGCTCCTATCAC   1020
1021  ATCGTCACTATCAGCCAGCCGGAGCTCGATGCGTAGGATGGTAAGGAATGGATGTTTCCA   1080
1081  AG   1082
```

Effect of ATRA on cAMP release in Cos-7 cells transfected with various cyclase stimulatory receptors

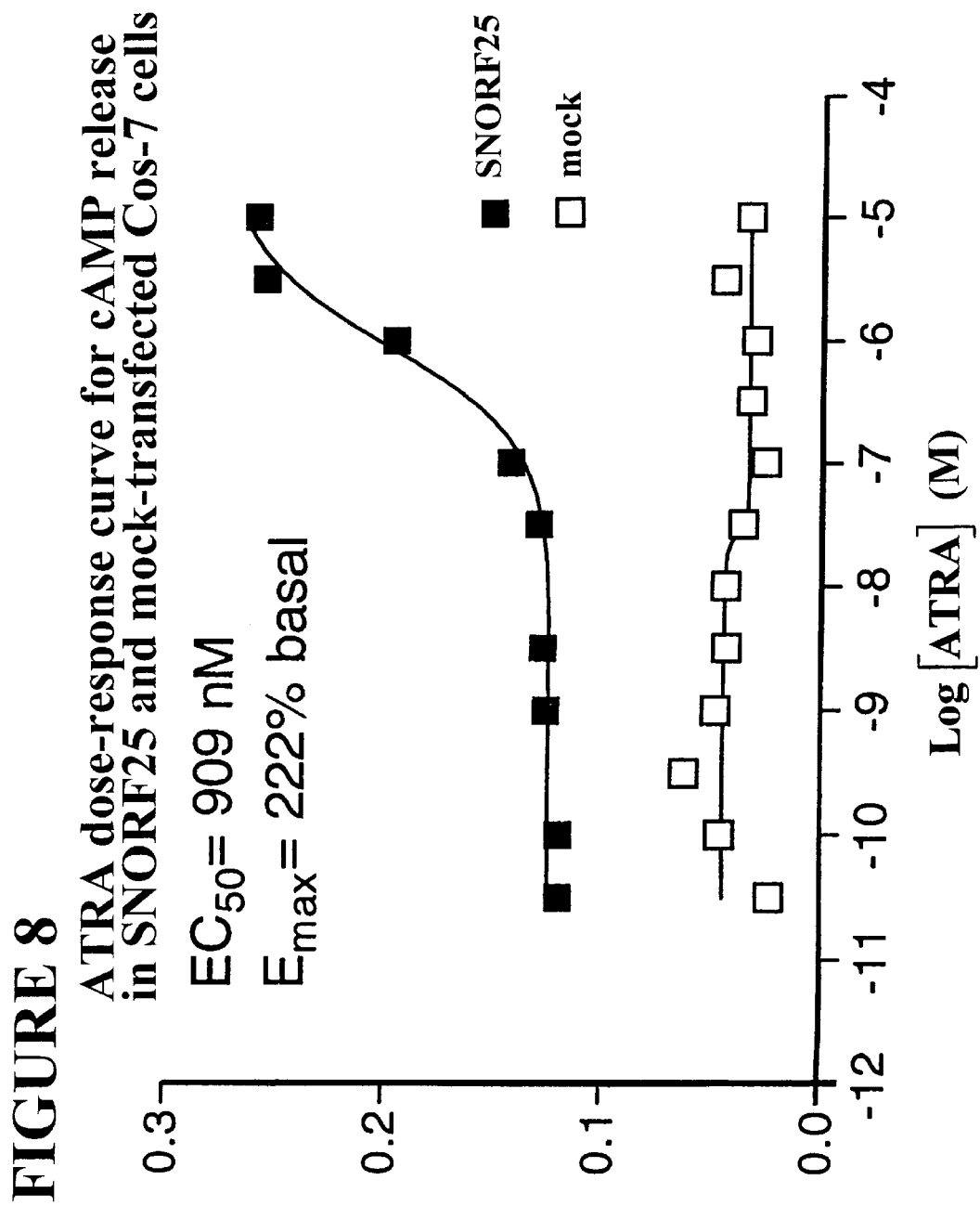

DNA ENCODING SNORF25 RECEPTOR

This application is a continuation-in-part of U.S. application Ser. No. 09/255,376, filed Feb. 22, 1999, the contents of which are hereby incorporated by reference into the subject application.

BACKGROUND OF THE INVENTION

Throughout this application various publications are referred to by partial citations within parentheses. Full citations for these publications may be found at the end of the specification immediately preceding the claims. The disclosures of these publications, in their entireties, are hereby incorporated by reference into this application in order to more fully describe the state of the art to which the invention pertains.

Neuroregulators comprise a diverse group of natural products that subverse or modulate communication in the nervous system. They include, but are not limited to, neuropeptides, amino acids, biogenic amines, lipids, and lipid metabolites, and other metabolic byproducts. Many of these neuroregulator substances interact with specific cell surface receptors, which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase.

Vitamin $A_1$ (all-trans-retinol) is oxidized to vitamin $A_1$ aldehyde (all-trans-retinal) by an alcohol dehydrogenase. All-trans-retinal is critical for the synthesis of rhodopsin in retinal cells, where it plays a key role in the visual system. All-trans-retinal can also be converted to all-trans-retinoic acid (ATRA) by aldehyde dehydrogenase and oxidase in other cell types (Bowman, W. C. and Rand, M. J., 1980).

Historically, ATRA and the other active metabolites of vitamin A, 9-cis-retinoic acid (9CRA), were thought to only mediate their cellular effects through the action of nuclear retinoic acid receptors (RARα, β, γ) and retinoid X receptors (RXRα, β, γ) (Mangelsdorf, D. J., et al,1994). These receptors are members of a superfamily of ligand-dependent transcription factors, which include the vitamin D receptor (VDR), thyroid hormone receptor (TR), and peroxisome proliferator activator receptors (PPAR). They form heterodimers and homodimers that bind to DNA response elements in the absence of ligand. In response to ligand binding the dimer changes conformation which leads to transactivation and regulation of transcription of a set(s) of cell type-specific genes (Mangelsdorf, D. J., et al,1994; Hofman, C. and Eichele, G., 1994; and Gudas, L. J. et al, 1994).

Since retinoic acid produces a wide variety of biological effects, it is not surprising that it is proposed to play an important role in various physiological and pathophysiological processes. Retinoids control critical physiological events including cell growth, differentiation, reproduction, metabolism, and hematopoiesis in a wide variety of tissues. At a cellular level, retinoids are capable of inhibiting cell proliferation, inducing differentiation, and inducing apoptosis (Breitman, T. et al, 1980; Sporn, M. and Roberts, A., 1984, and Martin, S., et al, 1990). These diverse effects of retinoid treatment prompted a series of investigations evaluating retinoids for cancer chemotherapy as well as cancer chemoprevention. Clinically, retinoids are used for the treatment of a wide variety of malignant diseases including: acute promyelocytic leukemia (APL), cutaneous T-cell malignancies, dermatological malignancies, squamous cell carcinomas of skin and of the cervix and neuroblastomas (Redfern, C. P. et al, 1995 for review). Retinoids have also been examined for their ability to suppress carcinogenesis and prevent development of invasive cancer. 13-cis retinoic acid reverses oral leukoplakia, the most common premalignant lesion of the aerodigestive tract, and is also used in the chemoprevention of bladder cancer (Sabichi, A. L. et al, 1998, for review). Also, 13-cis retinoic acid treatment as adjuvant therapy after surgery and radiation in head and neck cancer caused a significant delay in the occurrence of second primary cancers (Gottardis, M. M. et al, 1996, for review).

Interestingly, retinoids also have an effect on pancreatic function. It has been demonstrated that retinoic acid (or retinol) is required for insulin secretion from isolated islets (Chertow, B. S., et al, 1987) and from RINm5F rat insulinoma cells (Chertow, B. S., et al, 1989). Retinoic acid may also have an effect on cell-to-cell adhesion and aggregation (Chertow, B. S., et al, 1983). In addition, a single intragastric administration of 9CRA (but not ATRA) induced a wave of DNA synthesis in the pancreatic acinar cells and in the proximal tubular epithelial cells of the kidneys (Ohmura, T., et al, 1997). Therefore, retinoic acid could play a role in the normal pancreatic function and possibly in the development of diabetes. There is also some evidence that retinoids could be useful in the treatment of pancreatic malignancies (El-Metwally, T. H. et al, 1999; Rosenwicz, S. et al, 1997; and Rosenwicz, S. et al, 1995).

Retinoids have been shown to affect epidermal cell growth and differentiation as well as sebaceous gland activity and exhibit immunomodulatory and anti-inflammatory properties. Therefore, retinoids have been increasingly used for treatment of a variety of skin disorders including: psoriasis and other hyperkeratotic and parakeratotic skin disorders, keratotic genodermatosis, severe acne and acne-related dermatoses, and also for therapy and/or chemoprevention of skin cancer and other neoplasia (Orfanos, C. E., et al, 1997 for review).

Retinoids are also involved in lung development. Fetal lung branching leading to development of the alveolar tree is accelerated by retinoic acid. Currently, prematurely delivered infants who have immature lungs are treated with vitamin A, but other applications may exist that require further investigation (Chytil, F., 1996).

Lastly, there is some evidence that suggests that retinoids may play a role in schizophrenia (Goodman, A. B. 1998) and Alzheimer's disease (Connor, M. J. and Sidell, N., 1997).

The extensive list of retinoid-mediated effects indicate that retinoic acid receptors (non-nuclear) are attractive as targets for therapeutic intervention for several disorders and would be useful in developing drugs with higher specificity and fewer side effects for a wide variety of diseases.

SUMMARY OF THE INVENTION

This invention provides an isolated nucleic acid encoding a mammalian SNORF25 receptor.

This invention further provides a purified mammalian SNORF25 receptor protein.

This invention also provides a vector comprising a nucleic acid in accordance with this invention.

This invention still further provides a cell comprising a vector in accordance with this invention.

This invention additionally provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF25 receptor, wherein the probe has a sequence complementary to a unique sequence present within one of the two strands of the nucleic acid encoding the mammalian SNORF25 receptor contained in plasmid pEXJT3T7-hSNORF25 (ATCC Accession No. 203495).

This invention further provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 1A–1B (SEQ ID NO: 1) or (b) the reverse complement thereof.

This invention provides an antisense oligonucleotide having a sequence capable of specifically hybridizing to RNA encoding a mammalian SNORF25 receptor, so as to prevent translation of such RNA.

This invention further provides an antisense oligonucleotide having a sequence capable of specifically hybridizing to genomic DNA encoding a mammalian SNORF25 receptor, so as to prevent transcription of such genomic DNA.

This invention also provides an antibody capable of binding to a mammalian SNORF25 receptor encoded by a nucleic acid in accordance with this invention.

Moreover, this invention provides an agent capable of competitively inhibiting the binding of an antibody in accordance with this invention to a mammalian SNORF25 receptor.

This invention still further provides a pharmaceutical composition comprising (a) an amount of an oligonucleotide in accordance with this invention capable of passing through a cell membrane and effective to reduce expression of a mammalian SNORF25 receptor and (b) a pharmaceutically acceptable carrier capable of passing through the cell membrane.

This invention also provides a pharmaceutical composition which comprises an amount of an antibody in accordance with this invention effective to block binding of a ligand to a human SNORF25 receptor and a pharmaceutically acceptable carrier.

This invention further provides a transgenic, nonhuman mammal expressing DNA encoding a mammalian SNORF25 receptor in accordance with this invention.

This invention still further provides a transgenic, nonhuman mammal comprising a homologous recombination knockout of a native mammalian SNORF25 receptor.

This invention further provides a transgenic, nonhuman mammal whose genome comprises antisense DNA complementary to DNA encoding a mammalian SNORF25 receptor in accordance with this invention so placed within such genome as to be transcribed into antisense mRNA which is complementary to and hybridizes with mRNA encoding the mammalian SNORF25 receptor so as to reduce translation of of such mRNA and expression of such receptor.

This invention provides a process for identifying a chemical compound which specifically binds to a mammalian SNORF25 receptor which comprises contacting cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

This invention further provides a process for identifying a chemical compound which specifically binds to a mammalian SNORF25 receptor which comprises contacting a membrane preparation from cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

This invention still further provides a process involving competitive binding for identifying a chemical compound which specifically binds to a mammalian SNORF25 receptor which comprises separately contacting cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

This invention further provides a process involving competitive binding for identifying a chemical compound which specifically binds to a mammalian SNORF25 receptor which comprises separately contacting a membrane preparation from cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound indicating that the chemical compound binds to the mammalian SNORF25 receptor.

This invention further provides a compound identified by one of the processes of this invention.

This invention provides a method of screening a plurality of chemical compounds not known to bind to a mammalian SNORF25 receptor to identify a compound which specifically binds to the mammalian SNORF25 receptor, which comprises (a)contacting cells transfected with, and expressing, DNA encoding the mammalian SNORF25 receptor with a compound known to bind specifically to the mammalian SNORF25 receptor; (b) contacting the cells of step (a) with the plurality of compounds not known to bind specifically to the mammalian SNORF25 receptor, under conditions permitting binding of compounds known to bind to the mammalian SNORF25 receptor; (c) determining whether the binding of the compound known to bind to the mammalian SNORF25 receptor is reduced in the presence of the plurality of compounds, relative to the binding of the compound in the absence of the plurality of compounds; and if so (d) separately determining the binding to the mammalian SNORF25 receptor of each compound included in the plurality of compounds, so as to thereby identify any compound included therein which specifically binds to the mammalian SNORF25 receptor.

This invention further provides a method of screening a plurality of chemical compounds not known to bind to a mammalian SNORF25 receptor to identify a compound which specifically binds to the mammalian SNORF25 receptor, which comprises (a) contacting a membrane preparation from cells transfected with, and expressing, DNA encoding the mammalian SNORF25 receptor with the plurality of compounds not known to bind specifically to the mammalian SNORF25 receptor under conditions permitting binding of compounds known to bind to the mammalian SNORF25 receptor; (b) determining whether the binding of a compound known to bind to the mammalian SNORF25 receptor is reduced in the presence of any compound within the plurality of compounds, relative to the binding of the compound in the absence of the plurality of compounds; and if so (c) separately determining the binding to the mammalian SNORF25 receptor of each compound included in the plurality of compounds, so as to thereby identify any compound included therein which specifically binds to the mammalian SNORF25 receptor.

This invention also provides a method of detecting expression of a mammalian SNORF25 receptor by detecting the presence of mRNA coding for the mammalian SNORF25 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF25 receptor by the cell.

This invention further provides a method of detecting the presence of a mammalian SNORF25 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF25 receptor on the surface of the cell.

This invention still further provides a method of determining the physiological effects of varying levels of activity of mammalian SNORF25 receptors which comprises producing a transgenic, nonhuman mammal in accordance with this invention whose levels of mammalian SNORF25 receptor activity are varied by use of an inducible promoter which regulates mammalian SNORF25 receptor expression.

This invention additionally provides a method of determining the physiological effects of varying levels of activity of mammalian SNORF25 receptors which comprises producing a panel of transgenic, nonhuman mammals in accordance with this invention each expressing a different amount of mammalian SNORF25 receptor.

Moreover, this invention provides a method for identifying an antagonist capable of alleviating an abnormality wherein the abnormality is alleviated by decreasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF25 receptor, the alleviation of such an abnormality identifying the compound as an antagonist.

This invention also provides an antagonist identified by the preceding method.

This invention further provides a composition, e.g. a pharmaceutical composition, comprising an antagonist according to this invention and a carrier, e.g. a pharmaceutically acceptable carrier.

This invention additionally provides a method of treating an abnormality in a subject wherein the abnormality is alleviated by decreasing the activity of a mammalian SNORF25 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist.

This invention further provides an agonist identified by the preceding method.

This invention still further provides a composition, e.g. a pharmaceutical composition, comprising an agonist according to this invention and a carrier, e.g. pharmaceutically acceptable carrier.

Moreover, this invention provides a method of treating an abnormality in a subject wherein the abnormality is alleviated by increasing the activity of a mammalian SNORF25 receptor which comprises administering to the subject an effective amount of the pharmaceutical composition according to this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF25 receptor and labeled with a detectable marker; (e) detecting labeled bands which have hybridized to the DNA encoding a mammalian SNORF25 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention also provides a method of preparing a purified mammalian SNORF25 receptor according to the invention which comprises: (a) culturing cells which express the mammalian SNORF25 receptor; (b) recovering the mammalian SNORF25 receptor from the cells; and (c) purifying the mammalian SNORF25 receptor so recovered.

This invention further provides a method of preparing the purified mammalian SNORF25 receptor according to the invention which comprises: (a) inserting a nucleic acid encoding the mammalian SNORF25 receptor into a suitable expression vector; (b) introducing the resulting vector into a suitable host cell; (c) placing the resulting host cell in suitable conditions permitting the production of the mammalian SNORF25 receptor; (d) recovering the mammalian SNORF25 receptor so produced; and optionally (e) isolating and/or purifying the mammalian SNORF25 receptor so recovered.

Furthermore, this invention provides a process for determining whether a chemical compound is a mammalian SNORF25 receptor agonist which comprises contacting cells transfected with and expressing DNA encoding the mammalian SNORF25 receptor with the compound under conditions permitting the activation of the mammalian SNORF25 receptor, and detecting any increase in mammalian SNORF25 receptor activity, so as to thereby determine whether the compound is a mammalian SNORF25 receptor agonist.

This invention also provides a process for determining whether a chemical compound is a mammalian SNORF25 receptor antagonist which comprises contacting cells transfected with and expressing DNA encoding the mammalian SNORF25 receptor with the compound in the presence of a known mammalian SNORF2S receptor agonist, under conditions permitting the activation of the mammalian SNORF25 receptor, and detecting any decrease in mammalian SNORF25 receptor activity, so as to thereby determine whether the compound is a mammalian SNORF25 receptor antagonist.

This invention still further provides a composition, for example a pharmaceutical composition, which comprises an amount of a mammalian SNORF25 receptor agonist determined by a process according to this invention effective to increase activity of a mammalian SNORF25 receptor and a carrier, for example, a pharmaceutically acceptable carrier.

Also, this invention provides a composition, for example a pharmaceutical composition, which comprises an amount of a mammalian SNORF25 receptor antagonist determined by a process according to this invention effective to reduce activity of a mammalian SNORF25 receptor and a carrier, for example, a pharmaceutically acceptable carrier.

This invention moreover provides a process for determining whether a chemical compound specifically binds to and activates a mammalian SNORF25 receptor, which comprises contacting cells producing a second messenger response and expressing on their cell surface the mammalian SNORF25 receptor, wherein such cells do not normally express the mammalian SNORF25 receptor, with the chemical compound under conditions suitable for activation of the mammalian SNORF25 receptor, and measuring the second messenger response in the presence and in the absence of the chemical compound, a change, e.g. an increase, in the second messenger response in the presence of the chemical compound indicating that the compound activates the mammalian SNORF25 receptor.

This invention still further provides a process for determining whether a chemical compound specifically binds to and inhibits activation of a mammalian SNORF25 receptor, which comprises separately contacting cells producing a second messenger response and expressing on their cell surface the mammalian SNORF25 receptor, wherein such cells do not normally express the mammalian SNORF25 receptor, with both the chemical compound and a second chemical compound known to activate the mammalian SNORF25 receptor, and with only the second chemical compound, under conditions suitable for activation of the mammalian SNORF25 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF25 receptor.

Further, this invention provides a compound determined by a process according to the invention and a composition, for example, a pharmaceutical composition, which comprises an amount of a mammalian SNORF25 receptor agonist determined to be such by a process according to the invention, effective to increase activity of the mammalian SNORF25 receptor and a carrier, for example, a pharmaceutically acceptable carrier.

This invention also provides a composition, for example, a pharmaceutical composition, which comprises an amount of a mammalian SNORF25 receptor antagonist determined to be such by a process according to the invention, effective to reduce activity of the mammalian SNORF25 receptor and a carrier, for example, a pharmaceutically acceptable carrier.

This invention yet further provides a method of screening a plurality of chemical compounds not known to activate a mammalian SNORF25 receptor to identify a compound which activates the mammalian SNORF25 receptor which comprises: (a) contacting cells transfected with and expressing the mammalian SNORF25 receptor with the plurality of compounds not known to activate the mammalian SNORF25 receptor, under conditions permitting activation of the mammalian SNORF25 receptor; (b) determining whether the activity of the mammalian SNORF25 receptor is increased in the presence of one or more the compounds; and if so (c) separately determining whether the activation of the mammalian SNORF25 receptor is increased by any compound included in the plurality of compounds, so as to thereby identify each compound which activates the mammalian SNORF25 receptor.

This invention provides a method of screening a plurality of chemical compounds not known to inhibit the activation of a mammalian SNORF25 receptor to identify a compound which inhibits the activation of the mammalian SNORF25 receptor, which comprises: (a) contacting cells transfected with and expressing the mammalian SNORF25 receptor with the plurality of compounds in the presence of a known mammalian SNORF25 receptor agonist, under conditions permitting activation of the mammalian SNORF25 receptor; (b) determining whether the extent or amount of activation of the mammalian SNORF25 receptor is reduced in the presence of one or more of the compounds, relative to the extent or amount of activation of the mammalian SNORF25 receptor in the absence of such one or more compounds; and if so (c) separately determining whether each such compound inhibits activation of the mammalian SNORF25 receptor for each compound included in the plurality of compounds, so as to thereby identify any compound included in such plurality of compounds which inhibits the activation of the mammalian SNORF25 receptor.

This invention also provides a composition, for example a pharmaceutical composition, comprising a compound identified by a method according to this invention in an amount effective to increase mammalian SNORF25 receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF25 receptor activity and a carrier, for example, a pharmaceutically acceptable carrier.

Furthermore, this invention provides a method of treating an abnormality in a subject wherein the abnormality is alleviated by increasing the activity of a mammalian SNORF25 receptor which comprises administering to the subject a compound which is a mammalian SNORF25 receptor agonist in an amount effective to treat the abnormality.

This invention additionally provides a method of treating an abnormality in a subject wherein the abnormality is alleviated by decreasing the activity of a mammalian SNORF25 receptor which comprises administering to the subject a compound which is a mammalian SNORF25 receptor antagonist in an amount effective to treat the abnormality.

This invention also provides a process for making a composition of matter which specifically binds to a mammalian SNORF25 receptor which comprises identifying a chemical compound using a process in accordance with this invention and then synthesizing the chemical compound or a novel structural and functional analog or homolog thereof.

This invention further provides a process for preparing a composition, for example, a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof.

BRIEF DESCRIPTION OF THE FIGURES

FIGS. 1A–1B

Nucleotide sequence including sequence encoding a human SNORF25 receptor (SEQ ID NO: 1). Putative open reading frames including the shortest open reading frame are indicated by underlining one start (ATG) codon (at positions 61–63) and the stop codon (at positions 1066–1068). In addition, partial 5' and 3' untranslated sequences are shown.

FIGS. 2A–2B

Deduced amino acid sequence (SEQ ID NO: 2) of the human SNORF25 receptor encoded by the longest open reading frame indicated in the nucleotide sequence shown in FIGS. 1A–1B (SEQ ID NO: 1). The seven putative transmembrane (TM) regions are underlined.

FIGS. 3A–3B

Nucleotide sequence including sequence encoding a rat SNORF25 receptor (SEQ ID NO: 3). Putative open reading frames including the shortest open reading frame are indicated by underlining one start (ATG) codon (at positions 49–51) and the stop codon (at positions 1054–1056). In addition, partial 5' and 3' untranslated sequences are shown.

FIGS. 4A–4B

Deduced amino acid sequence (SEQ ID NO: 4) of the rat SNORF25 receptor encoded by the longest open reading frame indicated in the nucleotide sequence shown in FIGS. 3A–3B (SEQ. ID NO: 3). The seven putative transmembrane (TM) regions are underlined.

FIG. 5

Comparison of basal cAMP levels of SNORF25-and mock-transfected CHO cells. SNORF25 or empty vector (mock) DNA was transfected into CHO cells as described in Materials and Methods. The transfectants were plated into 96-well plates, and assayed for cAMP release as described. The results of a representative experiment are shown.

FIG. 6

Modulation of cAMP release by ATRA, vitamin A1 and forskolin in SNORF25-expressing and mock-transfected CHO cells. The transfectants were plated into 96-well plates, challenged with 10 $\mu$M concentrations of drugs and assayed for cAMP release as described. The results of a representative experiment involving known cyclase stimulatory receptors are shown. Results are means ±S.E.M of triplicate determinations with the exception of vitamin $A_1$ which is a single point. Results are normalized to % basal cAMP release.

FIG. 7

Specificity of ATRA cAMP response in Cos-7 cells. The transfectants were plated into 96-well plates, challenged with 10 $\mu$M concentrations of ATRA and assayed for cAMP release as described. The results of a representative experiment are shown. Results are means ±S.E.M of triplicate determinations.

FIG. 8

ATRA Dose-response curve in transiently-transfected Cos-7 cells. A representative example of dose-response effect of ATRA to increase cAMP release in SNORF25- (■) and mock- (□) transfected cells.

FIGS. 9A–9C

Figure 9A:
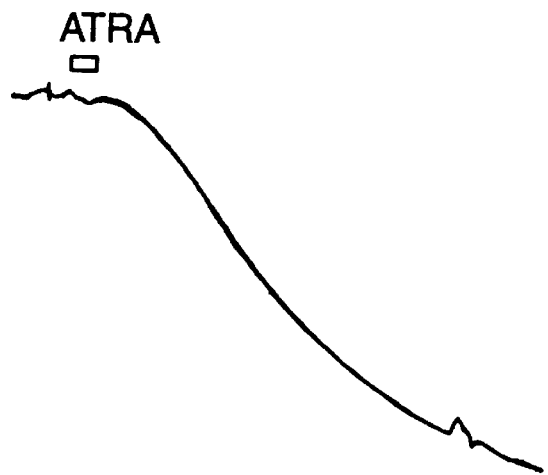
Figure 9B:
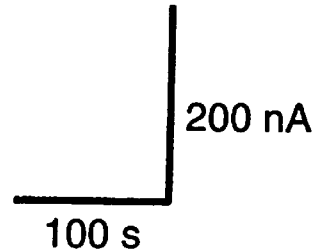
Figure 9C:
Figure 10:
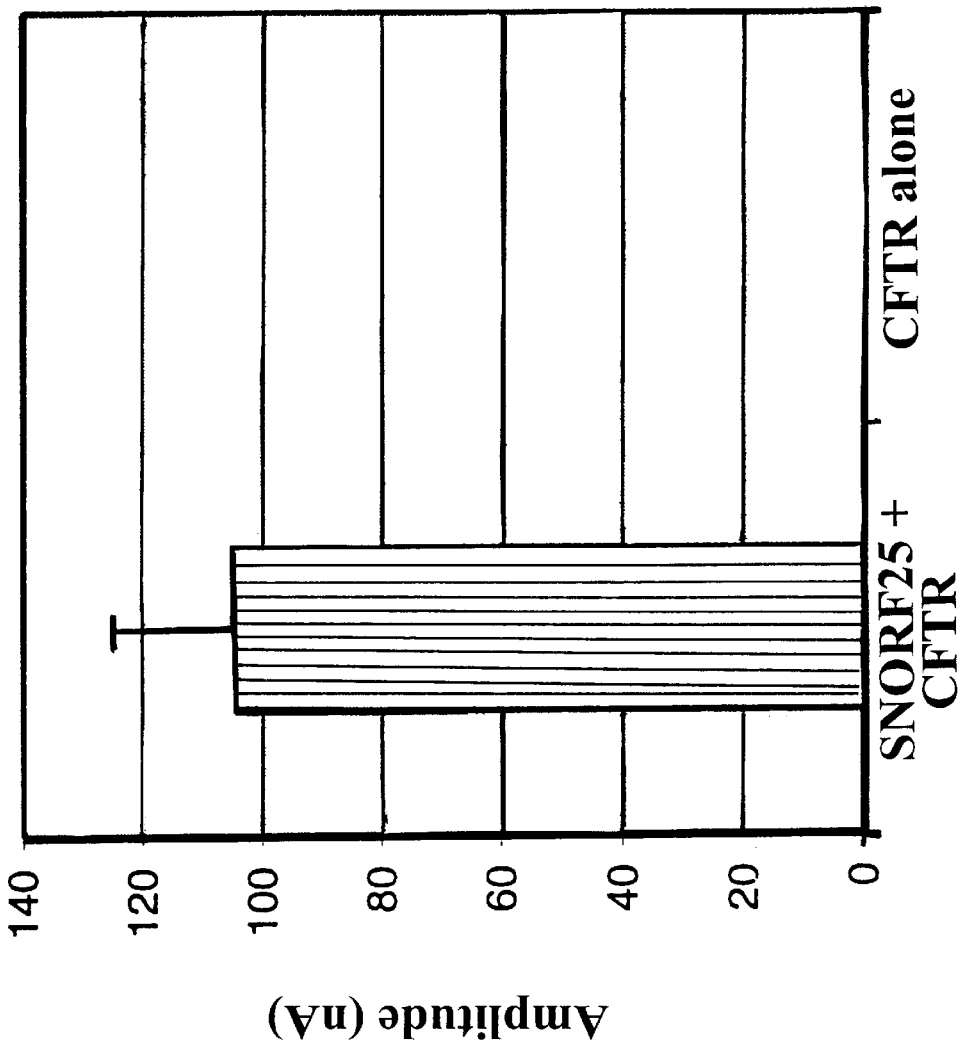

Stimulation of CFTR by ATRA in ooctyes expressing SNORF25. Voltage clamp recording from oocyte previously injected with SNORF25 receptor mRNA and CFTR (FIG. 9A), and from control (CFTR alone) oocyte (FIG. 9B). Application of epinephrine (1 $\mu$M) evokes a similar current in other oocytes expressing the B2 adrenergic receptor (B2AR) and CFTR (FIG. 9C). Holding potential was −70 mV for all recordings.

FIG. 10

Mean current amplitudes stimulated by ATRA (10 $\mu$M) in control (CFTR alone) ooctyes (n=16) and oocytes injected with mRNA encoding SNORF25 and CFTR (n=17).

DETAILED DESCRIPTION OF THE INVENTION

This invention provides a recombinant nucleic acid comprising a nucleic acid encoding a mammalian SNORF25 receptor, wherein the mammalian receptor-encoding nucleic acid hybridizes under high stringency conditions to (a) a nucleic acid encoding a human SNORF25 receptor and having a sequence identical to the sequence of the human SNORF25 receptor-encoding nucleic acid contained in plasmid pEXJT3T7-hSNORF25 (ATCC Accession No. 203495) or (b) a nucleic acid encoding a rat SNORF25 receptor and having a sequence identical to the sequence of the rat SNORF25 receptor-encoding nucleic acid contained in plasmid pcDNA3.1-rSNORF25 (ATCC Accession No. 203494).

This invention further provides a recombinant nucleic acid comprising a nucleic acid encoding a human SNORF25 receptor, wherein the human SNORF25 receptor comprises an amino acid sequence identical to the sequence of the human SNORF25 receptor encoded by the shortest open reading frame indicated in FIGS. 1A–1B (SEQ ID NO: 1).

This invention also provides a recombinant nucleic acid comprising a nucleic acid encoding a rat SNORF25 receptor, wherein the rat SNORF25 receptor comprises an amino acid sequence identical to the sequence of the rat SNORF25 receptor encoded by the shortest open reading frame indicated in FIGS. 3A–3B (SEQ ID NO: 3).

Plasmid pEXJT3T7-hSNORF25 and plasmid pcDNA3.1-rSNORF25 were both deposited on Nov. 24, 1998, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 203495 and 203494, respectively.

Hybridization methods are well known to those of skill in the art. For purposes of this invention, hybridization under high stringency conditions means hybridization performed at 40° C. in a hybridization buffer containing 50% formamide, 5× SSC, 7 mM Tris, 1× Denhardt's, 25 µg/ml salmon sperm DNA; wash at 50° C. in 0.1× SSC, 0.1% SDS.

Throughout this application, the following standard abbreviations are used to indicate specific nucleotide bases:

A=adenine
G=guanine
C=cytosine
T=thymine
M=adenine or cytosine
R=adenine or guanine
W=adenine or thymine
S=cytosine or guanine
Y=cytosine or thymine
K=guanine or thymine
V=adenine, cytosine, or guanine (not thymine)
H=adenine, cytosine, or thymine (not cytosine)
B=cytosine, guanine, or thymine (not adenine)
N=adenine, cytosine, guanine, or thymine (or other modified base such as inosine)
I=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

It is possible that the mammalian SNORF25 receptor gene contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns, et al., 1996; Chu, et al., 1996). Such variants may exhibit pharmacologic properties differing from the polypeptide encoded by the original gene.

This invention provides splice variants of the mammalian SNORF25 receptors disclosed herein. This invention further provides alternate translation initiation sites and alternately spliced or edited variants of nucleic acids encoding the SNORF25 receptors in accordance with this invention.

This invention also contemplates recombinant nucleic acids which comprise nucleic acids encoding naturally occurring allelic variants of the SNORF25 receptors disclosed herein.

The nucleic acids of the subject invention also include nucleic acid analogs of the human SNORF25 receptor genes, wherein the human SNORF25 receptor gene comprises the nucleic acid sequence shown in FIGS. 1A–1B or contained in plasmid pEXJT3T7-hSNORF25 (ATCC Accession No. 203495). Nucleic acid analogs of the human SNORF25 receptor genes differ from the human SNORF25 receptor genes described herein in terms of the identity or location of one or more nucleic acid bases (deletion analogs containing less than all of the nucleic acid bases shown in FIGS. 1A–1B or contained in plasmid pEXJT3T7-hSNORF25 (ATCC Accession No. 203495), substitution analogs wherein one or more nucleic acid bases shown in FIGS. 1A–1B or contained in plasmid pEXJT3T7-hSNORF25 (ATCC Accession No. 203495), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 1A–1B or contained in plasmid pEXJT3T7-hSNORF25 (ATCC Accession No. 203495). In one embodiment of the present invention, the nucleic acid analog encodes a protein which has an amino acid sequence identical to that shown in FIGS. 2A–2B or encoded by the nucleic acid sequence contained in plasmid pEXJT3T7-hSNORF25 (ATCC Accession No. 203495). In another embodiment, the nucleic acid analog encodes a protein having an amino acid sequence which differs from the amino acid sequences shown in FIGS. 2A–2B or encoded by the nucleic acid contained in plasmid pEXJT3T7-hSNORF25 (ATCC Accession No. 203495). In a further embodiment, the protein encoded by the nucleic acid analog has a function which is the same as the function of the receptor proteins having the amino acid sequence shown in FIGS. 2A–2B. In another embodiment, the function of the protein encoded by the nucleic acid analog differs from the function of the receptor protein having the amino acid sequence shown in FIGS. 2A–2B. In another embodiment, the variation in the nucleic acid sequence occurs within the transmembrane (TM) region of the protein. In a further embodiment, the variation in the nucleic acid sequence occurs outside of the TM region.

Figure 4A:
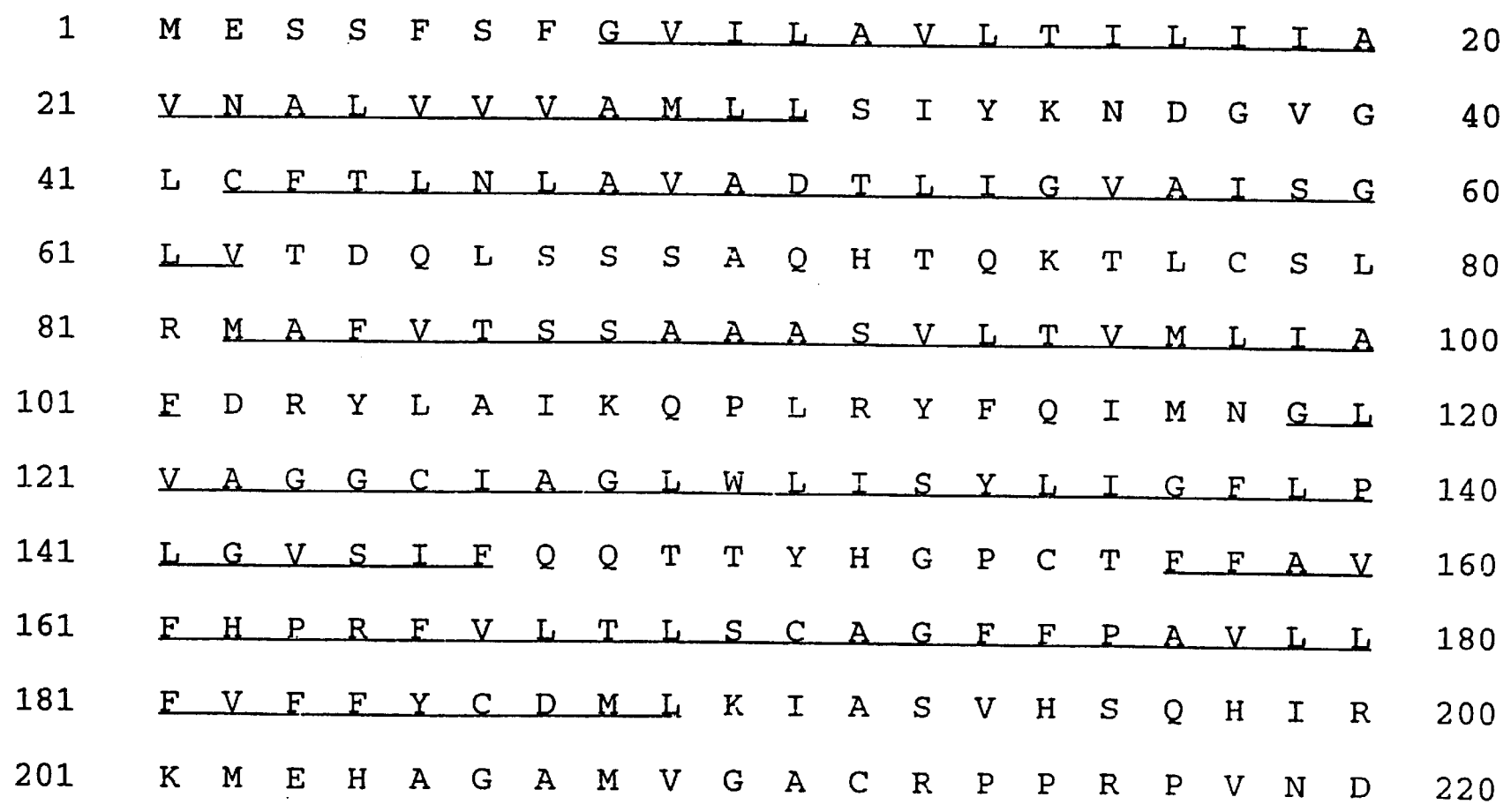
Figure 4B:
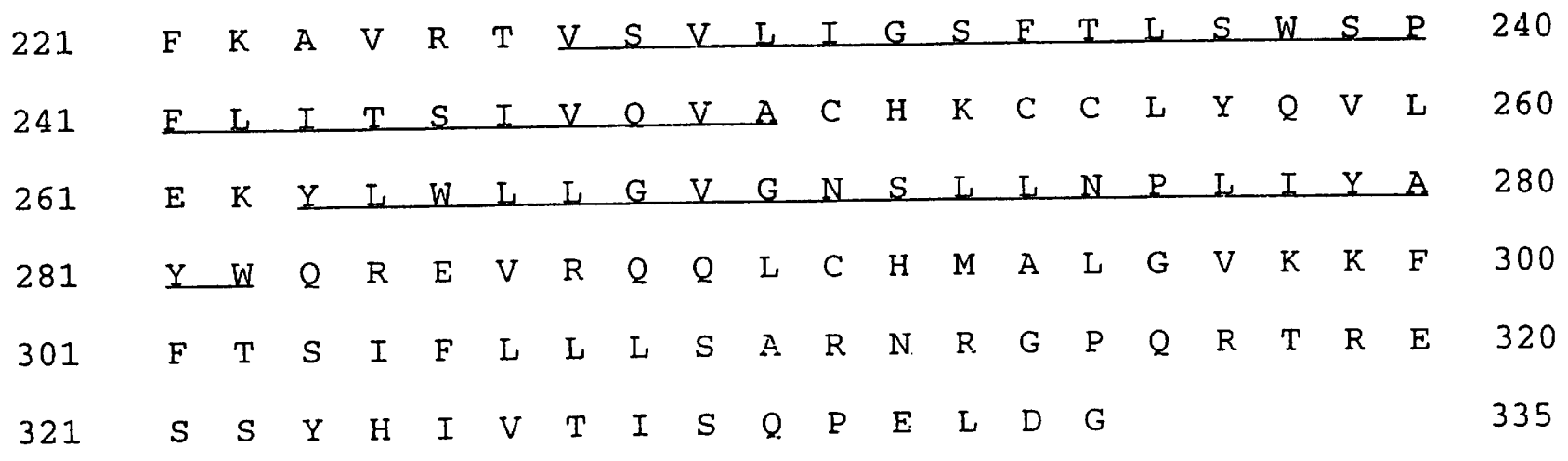

The nucleic acids of the subject invention also include nucleic acid analogs of the rat SNORF25 receptor genes, wherein the rat SNORF25 receptor gene comprises the nucleic acid sequence shown in FIGS. 3A–3B or contained in plasmid pcDNA3.1-rSNORF25 (ATCC Accession No. 203494). Nucleic acid analogs of the rat SNORF25 receptor genes differ from the rat SNORF25 receptor genes described herein in terms of the identity or location of one or more nucleic acid bases (deletion analogs containing less than all of the nucleic acid bases shown in FIGS. 3A–3B or contained in plasmid pcDNA3.1-rSNORF25 (ATCC Accession No. 203494) substitution analogs wherein one or more nucleic acid bases shown in FIGS. 3A–3B or contained in plasmid pcDNA3.1-rSNORF25 (ATCC Accession No. 203494), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIG. 3A–3B or contained in plasmid pcDNA3.1-rSNORF25 (ATCC Accession No. 203494). In one embodiment of the present invention, the nucleic acid analog encodes a protein which has an amino acid sequence identical to that shown in FIGS. 4A–4B or encoded by the nucleic acid sequence contained in plasmid pcDNA3.1-rSNORF25 (ATCC Accession No. 203494). In another embodiment, the nucleic acid analog encodes a protein having an amino acid sequence which differs from the amino acid sequences shown in FIGS. 4A–4B or encoded by the nucleic acid contained in plasmid pcDNA3.1-rSNORF25 (ATCC Accession No. 203494). In a further embodiment, the protein encoded by the nucleic acid analog has a function which is the same as the function of the receptor proteins having the amino acid sequence shown in FIGS. 4A–4B. In another embodiment, the function of the protein encoded by the nucleic acid analog differs from the function of the receptor protein having the amino acid sequence shown in FIGS. 4A–4B. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA. Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 1A–1B (SEQ ID NO: 1) or the nucleotide sequence contained in the plasmid pEXJT3T7-hSNORF25 (ATCC Accession No. 203495), that is, a nucleotide sequence which is translated into the same amino acid sequence.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 3A–3B (SEQ ID NO: 3) or the nucleotide sequence contained in the plasmid pcDNA3.1-rSNORF25 (ATCC Accession No. 203494), that is, a nucleotide sequence which is translated into the same amino acid sequence.

This invention also encompasses DNAs and cDNAs which encode amino acid sequences which differ from those of the polypeptides according to this invention, but which should not produce phenotypic changes. Alternately, this invention also encompasses DNAs, cDNAs, and RNAs which hybridize with the DNA, cDNA, and RNA according to the subject invention. Hybridization methods are well known to those of skill in the art.

The nucleic acids according to the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (Spurney, R. F. et al. (1997); Fong, T. M. et al. (1995); Underwood, D. J. et al. (1994); Graziano, M. P. et al. (1996); Guan X. M. et al. (1995)).

The modified polypeptides according to this invention may be transfected into cells either transiently or stably using methods well-known in the art, examples of which are disclosed herein. This invention also provides binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated nucleic acid encoding species homologs of the SNORF25 receptors encoded by the nucleic acid sequence shown in FIGS. 1A–1B (SEQ ID NO: 1) or encoded by the plasmid pEXJT3T7-hSNORF2S (ATCC Accession No. 203495). In one embodiment, the nucleic acid encodes a mammalian SNORF25 receptor homolog which has substantially the same amino acid sequence as does the SNORF25 receptor encoded by the plasmid pEXJT3T7-hSNORF25 (ATCC Accession No. 203495). In another embodiment, the nucleic acid encodes a mammalian SNORF25 receptor homolog which has above 75% amino acid identity to the SNORF25 receptor encoded by the plasmid pEXJT3T7-hSNORF25 (ATCC Accession No. 203495); preferably above 85% amino acid identity to the SNORF25 receptor encoded by the plasmid pEXJT3T7-hSNORF25 (ATCC Accession No. 203495); most preferably above 95% amino acid identity to the SNORF25 receptor encoded by the plasmid pEXJT3T7-hSNORF25 (ATCC Accession No. 203495). In another embodiment, the mammalian SNORF25 receptor homolog has above 70% nucleic acid identity to the SNORF25 receptor gene contained in plasmid pEXJT3T7-hSNORF25 (ATCC Accession No. 203495); preferably above 80% nucleic acid identity to the SNORF25 receptor gene contained in the plasmid pEXJT3T7-hSNORF25 (ATCC Accession No. 203495); more preferably above 90% nucleic acid identity to the SNORF25 receptor gene contained in the plasmid pEXJT3T7-hSNORF25 (ATCC Accession No. 203495). Examples of methods for isolating and purifying species homologs are described elsewhere (e.g., U.S. Pat. No. 5,602,024, WO94/14957, WO97/26853, WO98/15570).

This invention also provides an isolated nucleic acid encoding species homologs of the SNORF25 receptors encoded by the nucleic acid sequence shown in FIGS. 3A–3B (SEQ ID NO: 3) or encoded by the plasmid pcDNA3.1-rSNORF25 (ATCC Accession No. 203494). In one embodiment, the nucleic acid encodes a mammalian SNORF25 receptor homolog which has substantially the same amino acid sequence as does the SNORF25 receptor encoded by the plasmid pcDNA3.1-rSNORF25 (ATCC Accession No. 203494). In another embodiment, the nucleic acid encodes a mammalian SNORF25 receptor homolog which has above 75% amino acid identity to the SNORF25 receptor encoded by the plasmid pcDNA3.1-rSNORF25 (ATCC Accession No. 203494); preferably above 85% amino acid identity to the SNORF25 receptor encoded by the plasmid pcDNA3.1-rSNORF25 (ATCC Accession No. 203494); most preferably above 95% amino acid identity to the SNORF25 receptor encoded by the plasmid pcDNA3.1-rSNORF25 (ATCC Accession No. 203494). In another embodiment, the mammalian SNORF25 receptor homolog has above 70% nucleic acid identity to the SNORF25 receptor gene contained in plasmid pcDNA3.1-rSNORF25 (ATCC Accession No. 203494); preferably above 80% nucleic acid identity to the SNORF25 receptor gene contained in the plasmid pcDNA3.1-rSNORF25 (ATCC Accession No. 203494); more preferably above 90% nucleic acid identity to the SNORF25 receptor gene contained in the plasmid pcDNA3.1-rSNORF25 (ATCC Accession No. 203494).

This invention provides an isolated nucleic acid encoding a modified mammalian SNORF25 receptor, which differs from a mammalian SNORF25 receptor by having an amino acid(s) deletion, replacement, or addition in the third intracellular domain.

This invention provides an isolated nucleic acid encoding a mammalian SNORF25 receptor. In one embodiment, the nucleic acid is DNA. In another embodiment, the DNA is cDNA. In another embodiment, the DNA is genomic DNA. In another embodiment, the nucleic acid is RNA. In another embodiment, the mammalian SNORF25 receptor is a human SNORF25 receptor. In another embodiment, the human SNORF25 receptor has an amino acid sequence identical to that encoded by the plasmid pEXJT3 T7-hSNORF25 (ATCC Accession No. 203495). In another embodiment, the human SNORF25 receptor has an amino acid sequence identical to the amino acid sequence shown in FIGS. 2A–2B (SEQ ID NO: 2).

In an embodiment, the mammalian SNORF25 receptor is a rat SNORF25 receptor. In another embodiment, the rat SNORF25 receptor has an amino acid sequence identical to that encoded by the plasmid pcDNA3.1-rSNORF25 (ATCC Accession No. 203494) . In another embodiment, the rat SNORF25 receptor has an amino acid sequence identical to the amino acid sequence shown in FIGS. 4A–4B (SEQ ID NO: 4).

This invention provides a purified mammalian SNORF25 receptor protein. In one embodiment, the SNORF25 receptor protein is a human SNORF25 receptor protein. In a further embodiment, the SNORF25 receptor protein is a rat SNORF25 receptor protein.

This invention provides a vector comprising a nucleic acid in accordance with this invention. This invention further provides a vector adapted for expression in a cell which comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell. In one embodiment, the vector is a baculovirus. In another embodiment, the vector is a plasmid.

This invention provides a plasmid designated pEXJT3T7-hSNORF25 (ATCC Accession No. 203495). This invention also provides a plasmid designated pcDNA3.1-rSNORF25 (ATCC Accession No. 203494).

This invention further provides any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising a vector in accordance with this invention. In one embodiment, the cell is a non-mammalian cell. In one embodiment, the non-mammalian cell is a Xenopus oocyte cell or a Xenopus melanophore cell. In another embodiment, the cell is a mammalian cell. In another embodiment, the cell is a COS-7 cell, a 293 human embryonic kidney cell, a NIH-3T3 cell, a LM(tk−) cell, a mouse Y1 cell, or a CHO cell. In another embodiment, the cell is an insect cell. In another embodiment, the insect cell is an Sf9 cell, an Sf21 cell or a Trichoplusia ni 5B-4 cell.

This invention provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF25 receptor, wherein the probe has a sequence complementary to a unique sequence present within one of the two strands of the nucleic acid encoding the mammalian SNORF25 receptor contained in plasmid pEXJT3T7-hSNORF25 (ATCC Accession No. 203495) or plasmid pcDNA3.1-rSNORF25 (ATCC Accession No. 203494).

This invention further provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 1A–1B (SEQ ID NO: 1) or (b) the reverse complement thereof. This invention also provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 3A–3B (SEQ ID NO: 3) or (b) the reverse complement thereof. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

The nucleic acids according to this invention may be used as probes to obtain homologous nucleic acids from other species and to detect the existence of nucleic acids having complementary sequences in samples.

The nucleic acids may also be used to express the receptors they encode in transfected cells.

The use of a constitutively active receptor encoded by SNORF25 either occurring naturally without further modification or after appropriate point mutations, deletions or the like, allows screening for antagonists and in vivo use of such antagonists to attribute a role to receptor SNORF25 without prior knowledge of the endogenous ligand.

Use of the nucleic acids further enables elucidation of possible receptor diversity and of the existence of multiple subtypes within a family of receptors of which SNORF25 is a member.

Finally, it is contemplated that this receptor will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, neurological disorders, neuromotor disorders, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatic hypertrophy, gastrointestinal disorders, nasal congestion, dermatological disorders such as psoriasis, allergies, Parkinson's disease, Alzheimer's disease, acute heart failure, angina disorders, delirium, dyskinesias such as Huntington's disease or Gille's de la Tourette's syndrome, among others and diagnostic assays for such conditions. This receptor may also serve as a valuable tool for designing drugs for chemoprevention.

Methods of transfecting cells e.g. mammalian cells, with such nucleic acid to obtain cells in which the receptor is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the SNORF25 receptor, as well as compounds which activate or inhibit activation of functional responses in such cells, and therefore are likely to do so in vivo. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention further provides an antibody capable of binding to a mammalian receptor encoded by a nucleic acid encoding a mammalian receptor. In one embodiment, the mammalian receptor is a human receptor. In a further embodiment, the mammalian receptor is a rat receptor. This invention also provides an agent capable of competitively inhibiting the binding of an antibody to a mammalian receptor. In one embodiment, the antibody is a monoclonal antibody or antisera.

Methods of preparing and employing antisense oligonucleotides, antibodies, nucleic acid probes and transgenic animals directed to the SNORF25 receptor are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention also provides an antisense oligonucleotide having a sequence capable of specifically hybridizing to RNA encoding a mammalian SNORF25 receptor, so as to prevent translation of such RNA. This invention further provides an antisense oligonucleotide having a sequence capable of specifically hybridizing to genomic DNA encoding a mammalian SNORF25 receptor, so as to prevent transcription of such genomic DNA. In one embodiment, the oligonucleotide comprises chemically modified nucleotides or nucleotide analogues.

This invention provides an antibody capable of binding to a mammalian SNORF25 receptor encoded by a nucleic acid in accordance with this invention. In one embodiment, the mammalian SNORF25 receptor is a human SNORF25 receptor. In a further embodiment, the mammalian SNORF25 receptor is a rat SNORF25 receptor.

Moreover, this invention provides an agent capable of competitively inhibiting the binding of an antibody in accordance with this invention to a mammalian SNORF25 receptor. In one embodiment, the antibody is a monoclonal antibody or antisera.

This invention still further provides a pharmaceutical composition comprising (a) an amount of an oligonucleotide in accordance with this invention capable of passing through a cell membrane and effective to reduce expression of a mammalian SNORF25 receptor and (b) a pharmaceutically acceptable carrier capable of passing through the cell membrane.

In one embodiment, the oligonucleotide is coupled to a substance which inactivates mRNA. In another embodiment, the substance which inactivates mRNA is a ribozyme. In another embodiment, the pharmaceutically acceptable carrier comprises a structure which binds to a mammalian SNORF25 receptor on a cell capable of being taken up by the cells after binding to the structure. In another embodiment, the pharmaceutically acceptable carrier is capable of binding to a mammalian SNORF25 receptor which is specific for a selected cell type.

This invention also provides a pharmaceutical composition which comprises an amount of an antibody in accordance with this invention effective to block binding of a ligand to a human SNORF25 receptor and a pharmaceutically acceptable carrier.

This invention further provides a transgenic, nonhuman mammal expressing DNA encoding a mammalian SNORF25 receptor in accordance with this invention. This invention provides a transgenic, nonhuman mammal comprising a homologous recombination knockout of a native mammalian SNORF25 receptor. This invention further provides a transgenic, nonhuman mammal whose genome comprises antisense DNA complementary to DNA encoding a mammalian SNORF25 receptor in accordance with this invention so placed within such genome as to be transcribed into antisense mRNA which is complementary to and hybridizes with mRNA encoding the mammalian SNORF25 receptor so as to reduce translation of such mRNA and expression of such receptor. In one embodiment, the DNA encoding the mammalian SNORF25 receptor additionally comprises an inducible promoter. In another embodiment, the DNA encoding the mammalian SNORF25 receptor additionally comprises tissue specific regulatory elements. In another embodiment, the transgenic, nonhuman mammal is a mouse.

This invention provides a process for identifying a chemical compound which specifically binds to a mammalian SNORF25 receptor which comprises contacting cells containing DNA encoding, and expressing on their cell surface, the mammalian SNORF25 receptor, wherein such cells do not normally express the mammalian SNORF2S receptor, with the compound under conditions suitable for binding, and detecting specific binding of the chemical compound to the mammalian SNORF25 receptor. This invention further provides a process for identifying a chemical compound which specifically binds to a mammalian SNORF25 receptor which comprises contacting a membrane preparation from cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

In one embodiment, the mammalian SNORF25 receptor is a human SNORF25 receptor. In another embodiment, the mammalian SNORF25 receptor has substantially the same amino acid sequence as the human SNORF25 receptor encoded by plasmid pEXJT3T7-hSNORF25 (ATCC Accession No. 203495). In another embodiment, the mammalian SNORF25 receptor has substantially the same amino acid sequence as that shown in FIGS. 2A–2B (SEQ ID NO: 2). In another embodiment, the mammalian SNORF25 receptor has the amino acid sequence shown in FIGS. 2A–2B (SEQ ID NO: 2).

In another embodiment, the mammalian SNORF25 receptor is a rat SNORF25 receptor. In another embodiment, the mammalian SNORF25 receptor has substantially the same amino acid sequence as the rat SNORF25 receptor encoded by plasmid pcDNA3.1-rSNORF25 (ATCC Accession No. 203494). In another embodiment, the mammalian SNORF25 receptor has substantially the same amino acid sequence as that shown in FIGS. 4A–4B (SEQ ID NO: 4). In another embodiment, the mammalian SNORF25 receptor has the amino acid sequence shown in FIGS. 4A–4B (SEQ ID NO: 4).

In one embodiment, the compound is not previously known to bind to a mammalian SNORF25 receptor. In one embodiment, the cell is an insect cell. In one embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is a compound not previously known to bind to a mammalian SNORF25 receptor. This invention provides a compound identified by the preceding process of this invention.

This invention still further provides a process involving competitive binding for identifying a chemical compound which specifically binds to a mammalian SNORF25 receptor which comprises separately contacting cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

This invention provides a process involving competitive binding for identifying a chemical compound which specifically binds to a mammalian SNORF25 receptor which comprises separately contacting a membrane preparation from cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

In one embodiment, the mammalian SNORF25 receptor is a human SNORF25 receptor. In another embodiment, the mammalian SNORF25 receptor is a rat SNORF25 receptor. In a further embodiment, the cell is an insect cell. In another embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is not previously known to bind to a mammalian SNORF25 receptor. This invention provides a compound identified by the preceding process of this invention.

This invention provides a method of screening a plurality of chemical compounds not known to bind to a mammalian SNORF25 receptor to identify a compound which specifically binds to the mammalian SNORF25 receptor, which comprises (a) contacting cells transfected with, and expressing, DNA encoding the mammalian SNORF25 receptor with a compound known to bind specifically to the mammalian SNORF25 receptor; (b) contacting the cells of step (a) with the plurality of compounds not known to bind specifically to the mammalian SNORF25 receptor, under conditions permitting binding of compounds known to bind to the mammalian SNORF25 receptor; (c) determining whether the binding of the compound known to bind to the mammalian SNORF25 receptor is reduced in the presence of the plurality of compounds, relative to the binding of the compound in the absence of the plurality of compounds; and if so (d) separately determining the binding to the mammalian SNORF25 receptor of each compound included in the plurality of compounds, so as to thereby identify any compound included therein which specifically binds to the mammalian SNORF25 receptor.

This invention provides a method of screening a plurality of chemical compounds not known to bind to a mammalian SNORF25 receptor to identify a compound which specifically binds to the mammalian SNORF25 receptor, which comprises (a) contacting a membrane preparation from cells transfected with, and expressing, DNA encoding the mammalian SNORF25 receptor with the plurality of compounds not known to bind specifically to the mammalian SNORF25 receptor under conditions permitting binding of compounds known to bind to the mammalian SNORF25 receptor; (b) determining whether the binding of a compound known to bind to the mammalian SNORF25 receptor is reduced in the presence of the plurality of compounds, relative to the binding of the compound in the absence of the plurality of compounds; and if so (c) separately determining the binding to the mammalian SNORF25 receptor of each compound included in the plurality of compounds, so as to thereby identify any compound included therein which specifically binds to the mammalian SNORF25 receptor.

In one embodiment, the mammalian SNORF25 receptor is a human SNORF25 receptor. In a further embodiment, the mammalian SNORF25 receptor is a rat SNORF25 receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk−) cell, a CHO cell, a mouse Y1 cell, or an NIH-3T3 cell.

This invention provides a method of detecting expression of a mammalian SNORF25 receptor by detecting the presence of mRNA coding for the mammalian SNORF25 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF25 receptor by the cell.

This invention provides a method of detecting the presence of a mammalian SNORF25 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF25 receptor on the surface of the cell.

This invention provides a method of determining the physiological effects of varying levels of activity of mammalian SNORF25 receptors which comprises producing a transgenic, nonhuman mammal in accordance with this invention whose levels of mammalian SNORF25 receptor activity are varied by use of an inducible promoter which regulates mammalian SNORF25 receptor expression.

This invention provides a method of determining the physiological effects of varying levels of activity of mammalian SNORF25 receptors which comprises producing a panel of transgenic, nonhuman mammals in accordance with this invention each expressing a different amount of mammalian SNORF25 receptor.

This invention provides a method for identifying an antagonist capable of alleviating an abnormality wherein the abnormality is alleviated by decreasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF25 receptor, the alleviation of such abnormality identifying the compound as an antagonist. In one embodiment, the mammalian SNORF25 receptor is a human SNORF25 receptor. In a further embodiment, the mammalian SNORF25 receptor is a rat SNORF25 receptor. The invention provides an antagonist identified by the preceding method according to this invention. This invention provides a composition, e.g. a pharmaceutical composition, comprising an antagonist according to this invention and a carrier, e.g. a pharmaceutically acceptable carrier. This invention provides a method of treating an abnormality in a subject wherein the abnormality is alleviated by decreasing the activity of a mammalian SNORF25 receptor which comprises administering to the subject an effective amount of the pharmaceutical composition according to this invention so as to thereby treat the abnormality.

This invention provides a method for identifying an agonist capable of alleviating an abnormality in a subject wherein the abnormality is alleviated by increasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In one embodiment, the mammalian SNORF25 receptor is a human SNORF25 receptor. In a further embodiment, the mammalian SNORF25 receptor is a rat SNORF25 receptor. This invention provides an agonist identified by the preceding method according to this invention. This invention provides a composition, e.g. a pharmaceutical composition, comprising an agonist identified by the method according to this invention and a carrier, e.g. a pharmaceutically acceptable carrier.

This invention provides a method of treating an abnormality in a subject wherein the abnormality is alleviated by increasing the activity of a mammalian SNORF25 receptor which comprises administering to the subject an effective amount of the pharmaceutical composition according to this invention so as to thereby treat the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF25 receptor and labeled with a detectable marker; (e) detecting labeled bands which have hybridized to the DNA encoding a mammalian SNORF25 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention provides a method of preparing a purified mammalian SNORF25 receptor according to this invention which comprises: (a) culturing cells which express the mammalian SNORF25 receptor; (b) recovering the mammalian SNORF25 receptor from the cells; and (c) purifying the mammalian SNORF25 receptor so recovered.

This invention provides a method of preparing the purified mammalian SNORF25 receptor according to this invention which comprises: (a) inserting a nucleic acid encoding the mammalian SNORF25 receptor into a suitable expression vector; (b) introducing the resulting vector into a suitable host cell; (c) placing the resulting host cell in suitable conditions permitting the production of the mammalian SNORF25 receptor; (d) recovering the mammalian SNORF25 receptor so produced; and optionally (e) isolating and/or purifying the mammalian SNORF25 receptor so recovered.

This invention provides a process for determining whether a chemical compound is a mammalian SNORF25 receptor agonist which comprises contacting cells transfected with and expressing DNA encoding the mammalian SNORF25 receptor with the compound under conditions permitting the activation of the mammalian SNORF25 receptor, and detecting any increase in mammalian SNORF25 receptor activity, so as to thereby determine whether the compound is a mammalian SNORF25 receptor agonist.

This invention provides a process for determining whether a chemical compound is a mammalian SNORF25 receptor antagonist which comprises contacting cells transfected with and expressing DNA encoding the mammalian SNORF25 receptor with the compound in the presence of a known mammalian SNORF25 receptor agonist, under conditions permitting the activation of the mammalian SNORF25 receptor, and detecting any decrease in mammalian SNORF25 receptor activity, so as to thereby determine whether the compound is a mammalian SNORF25 receptor antagonist.

In one embodiment, the mammalian SNORF25 receptor is a human SNORF25 receptor. In another embodiment, the mammalian SNORF25 receptor is a rat SNORF25 receptor.

This invention provides a composition, for example a pharmaceutical composition, which comprises an amount of a mammalian SNORF25 receptor agonist determined by a process according to this invention effective to increase activity of a mammalian SNORF25 receptor and a carrier, for example, a pharmaceutically acceptable carrier. In one embodiment, the mammalian SNORF25 receptor agonist is not previously known.

This invention provides a composition, for example a pharmaceutical composition, which comprises an amount of a mammalian SNORF25 receptor antagonist determined by a process according to this invention effective to reduce activity of a mammalian SNORF25 receptor and a carrier, for example, a pharmaceutically acceptable carrier. In one embodiment, the mammalian SNORF25 receptor antagonist is not previously known.

This invention provides a process for determining whether a chemical compound specifically binds to and activates a mammalian SNORF25 receptor, which comprises contacting cells producing a second messenger response and expressing on their cell surface the mammalian SNORF25 receptor, wherein such cells do not normally express the mammalian SNORF25 receptor, with the chemical compound under conditions suitable for activation of the mammalian SNORF25 receptor, and measuring the second messenger response in the presence and in the absence of the chemical compound, a change, e.g. an increase, in the second messenger response in the presence of the chemical compound indicating that the compound activates the mammalian SNORF25 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is an increase in cAMP accumulation.

This invention provides a process for determining whether a chemical compound specifically binds to and inhibits activation of a mammalian SNORF25 receptor, which comprises separately contacting cells producing a second messenger response and expressing on their cell surface the mammalian SNORF25 receptor, wherein such cells do not normally express the mammalian SNORF25 receptor, with both the chemical compound and a second chemical compound known to activate the mammalian SNORF25 receptor, and with only the second chemical compound, under conditions suitable for activation of the mammalian SNORF25 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF25 receptor.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian SNORF25 receptor is a human SNORF25 receptor. In a further embodiment, the mammalian SNORF25 receptor is a rat SNORF25 receptor. In another embodiment, the cell is an insect cell. In another embodiment, the cell is a mammalian cell. In another embodiment, the mammalian cell is nonneuronal in origin. In another embodiment, the nonneuronal cell is a COS-7 cell, CHO cell, 293 human embryonic kidney cell, NIH-3T3 cell or LM(tk–) cell. In another embodiment, the compound is not previously known to bind to a mammalian SNORF25 receptor.

This invention provides a compound determined by a process according to this invention and a composition, for example, a pharmaceutical composition, which comprises an amount of a mammalian SNORF25 receptor agonist determined to be such by a process according to this invention effective to increase activity of the mammalian SNORF25 receptor and a carrier, for example, a pharmaceutically acceptable carrier. In one embodiment, the mammalian SNORF25 receptor agonist is not previously known.

This invention provides a composition, for example, a pharmaceutical composition, which comprises an amount of a mammalian SNORF25 receptor antagonist determined to be such by a process according to this invention, effective to reduce activity of the mammalian SNORF25 receptor and a carrier, for example, a pharmaceutically acceptable carrier. In one embodiment, the mammalian SNORF25 receptor antagonist is not previously known.

This invention provides a method of screening a plurality of chemical compounds not known to activate a mammalian SNORF25 receptor to identify a compound which activates the mammalian SNORF25 receptor which comprises: (a) contacting cells transfected with and expressing the mammalian SNORF25 receptor with the plurality of compounds not known to activate the mammalian SNORF25 receptor, under conditions permitting activation of the mammalian SNORF25 receptor; (b) determining whether the activity of the mammalian SNORF25 receptor is increased in the presence of one or more of the compounds; and if so (c) separately determining whether the activation of the mammalian SNORF25 receptor is increased by any compound included in the plurality of compounds, so as to thereby identify each compound which activates the mammalian SNORF25 receptor. In one embodiment, the mammalian SNORF25 receptor is a human SNORF25 receptor. In a further embodiment, the mammalian SNORF25 receptor is a rat SNORF25 receptor.

This invention provides a method of screening a plurality of chemical compounds not known to inhibit the activation of a mammalian SNORF25 receptor to identify a compound which inhibits the activation of the mammalian SNORF25 receptor, which comprises: (a) contacting cells transfected with and expressing the mammalian SNORF25 receptor with the plurality of compounds in the presence of a known mammalian SNORF25 receptor agonist, under conditions permitting activation of the mammalian SNORF25 receptor; (b) determining whether the extent or amount of activation of the mammalian SNORF25 receptor is reduced in the presence of one or more of the compounds, relative to the extent or amount of activation of the mammalian SNORF25 receptor in the absence of such one or more compounds; and if so (c) separately determining whether each such compound inhibits activation of the mammalian SNORF25 receptor for each compound included in the plurality of compounds, so as to thereby identify any compound included in such plurality of compounds which inhibits the activation of the mammalian SNORF25 receptor.

In one embodiment, the mammalian SNORF25 receptor is a human SNORF25 receptor. In a further embodiment, the mammalian SNORF25 receptor is a rat SNORF25 receptor. In another embodiment, wherein the cell is a mammalian cell. In another embodiment, the mammalian cell is non-neuronal in origin. In another embodiment, the non-neuronal cell is a COS-7 cell, a 293 human embryonic kidney cell, a LM(tk−) cell or an NIH-3T3 cell.

This invention provides a composition, for example a pharmaceutical composition, comprising a compound identified by a method according to this invention in an amount effective to increase mammalian SNORF25 receptor activity and a carrier, for example, a pharmaceutically acceptable carrier.

This invention provides a composition, for example, a pharmaceutical composition, comprising a compound identified by a method according to this invention in an amount effective to decrease mammalian SNORF25 receptor activity and a carrier, for example, a pharmaceutically acceptable carrier.

This invention provides a method of treating an abnormality in a subject wherein the abnormality is alleviated by increasing the activity of a mammalian SNORF25 receptor which comprises administering to the subject a compound which is a mammalian SNORF25 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a sensory transmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a method of treating an abnormality in a subject wherein the abnormality is alleviated by decreasing the activity of a mammalian SNORF25 receptor which comprises administering to the subject a compound which is a mammalian SNORF25 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a somatosensory neurotransmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a process for making a composition of matter which specifically binds to a mammalian SNORF25 receptor which comprises identifying a chemical compound using a process in accordance with this invention and then synthesizing the chemical compound or a novel structural and functional analog or homolog thereof. In one embodiment, the mammalian SNORF25 receptor is a human SNORF25 receptor. In another embodiment, the mammalian SNORF25 receptor is a rat SNORF25 receptor.

This invention provides a process for preparing a composition, for example, a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian SNORF25 receptor is a human SNORF25 receptor. In another embodiment, the mammalian SNORF25 receptor is a rat SNORF25 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Mixed Oligonucleotide Primed Amplification of cDNA (MOPAC)

Mixed Oligonucleotide Primed Amplification of cDNA (MOPAC) was performed on several DNA templates including: rat genomic DNA, cDNA reverse-transcribed from mRNA isolated from the GH1 cell line, and the Rin14b cell line. The MOPAC reaction was performed using Taq DNA polymerase (Boehringer-Mannheim, Indianapolis, Ind.) and the following degenerate oligonucleotides: JAB55, designed based on the third transmembrane domain of the galanin, somatostatin, and opiate receptor families; and TL1020, designed based on the $7^{th}$ transmembrane domain of the galanin receptor family.

The conditions for the MOPAC PCR reaction were as follows: 3 minute hold at 94° C.; 10 cycles of 1 minute at 94° C., 1 minute 45 seconds at 44° C., 2 minutes at 72° C.; 30 cycles of 94° C. for 1 minute, 49° C. for 1 minute 45 seconds, 2 minutes at 72° C.; 4 minute hold at 72° C.; 4° C. hold until ready for agarose gel electrophoresis.

The products were run on a 1% agarose TAE gel and bands of the expected size (~500–600 bp) were cut from the gel, purified using the QIAQUICK gel extraction kit (QIAGEN, Chatsworth, Calif.), and subcloned into the TA cloning vector (Invitrogen, San Diego, Calif.). White (insert-containing) colonies were picked and subjected to PCR using pCR2.1 vector primers JAB1 and JAB2 using the following protocol: 94° C. hold for 3 minutes; 35 cycles of 94° C. for 1 minute, 68° C. for 1 minute 15 seconds; 2 minute hold at 68° C., 4° C. hold until the products were ready for purification. PCR products were purified by isopropanol precipitation (10 µl PCR product, 18 µl low TE, 10.5 µl 2M $NaClO_4$, and 21.5 µl isopropanol) and sequenced using the ABI Big Dye cycle sequencing protocol and ABI 377 sequencers (ABI, Foster City, Calif.). One of these PCR products, later named SNORF25, was determined to be a novel G protein-coupled receptor-like sequence based on database searches and its homology to other known G protein-coupled receptors (~29% identity to the known receptors dopamine D1, beta-adrenergic 2b and 5-HT1f; 34% identity to the 5-HT4l receptor).

5' and 3' RACE

To determine the full-length coding sequence of SNORF25, the Clontech Marathon cDNA Amplification kit (Clontech, Palo Alto, Calif.) for 5'/3' Rapid Amplification of cDNA ends (RACE) was utilized. Total RNA from Rin14b cells was PolyA⁺-selected using a FastTrack mRNA Isolation Kit (Invitrogen). For 5'RACE, double-stranded cDNA was synthesized from 1 µg polyA⁺ RNA using primer JAB73, a reverse primer from the putative fifth transmembrane domain of the PCR fragment described above (SNORF25). Adaptor ligation and nested PCR were performed according to the Marathon cDNA Amplification protocol using Advantage Klentaq Polymerase (Clontech, Palo Alto, Calif.). The initial PCR was performed on a 50-fold dilution of the ligated cDNA using the supplier's Adaptor Primer 1 and JAB71, a reverse primer from the 5'end of the fifth transmembrane domain of the PCR fragment described above. One µl of this initial PCR reaction was re-amplified using the Adaptor Primer 2 and JAB69, a reverse primer just downstream of the fourth transmembrane domain. The conditions for PCR were 1 minute at 94° C.; 5 cycles of 94° C. for 15 seconds and 72° C. for 1 minute 30 seconds; 5 cycles of 94° C. for 15 seconds and 70° C. for 1 minute 30 seconds; 22 cycles of 94° C. for 15 seconds and 68° C. for 1 minute 30 seconds; 68° C. hold for 5 minutes, and 4° C. hold until the products were ready for analysis. A 600 bp fragment from the nested PCR was isolated from a 1% agarose TAE gel using the QIAQUICK kit and sequenced using ABI 377 sequencers and BigDye termination cycle sequencing as described above. Sequences were analyzed using the Wisconsin Package (GCG, Genetics Computer Group, Madison, Wis.).

For 3' RACE, double stranded cDNA was synthesized from 1 µg polyA⁻ RNA using the cDNA synthesis primer CDS supplied with the Marathon cDNA Amplification Kit (Clontech). PCR conditions for the 3' RACE reactions were similar to the 5' RACE reactions, except that JAB74 and JAB72, forward primers from the sequence located between the fifth and sixth transmembrane domains of the novel PCR fragment from MOPAC described above, were used in place of JAB 71 and JAB73, respectively. A 1.4 kb fragment from the nested PCR was isolated from a 1% agarose TAE gel using the QIAQUICK gel purification kit (QIAGEN) and sequenced as above.

After determining the full-length coding sequence of this receptor sequence, the entire coding region was amplified from Rin14b cell line cDNA and rat genomic DNA using the Expand Long PCR system (Boehringer-Mannheim). The primers for this reaction were specific to the 5' and 3' untranslated regions of SNORF25 with BamHI and HindIII restriction sites incorporated into the 5' ends of the 5' (JAB86) and 3' (JAB84) primers, respectively. The products from this reaction were then digested with BamHI and HindIII, subcloned into the BamHI/HindIII site of the expression vector pcDNA3.1 (-), and sequenced in both directions using vector- and gene-specific primers. Double-stranded sequence from the Rin14b-cloned SNORF25 product agreed with the sequence of the same gene amplified from rat genomic DNA. This receptor/expression vector construct of rat SNORF25 in pcDNA3.1(-) was named pcDNA3.1-rSNORF25.

Homology cloning of the human homolog of SNORF25

To clone the human homolog of SNORF25, two oligonucleotide probes were designed based on the second (BB426) and fifth (BB427) transmembrane domains (TMs) of the rat SNORF25 sequence, and used to probe a human genomic cosmid library (Clontech). Both primers were end-labeled with $\alpha^{32}$P-dATP and terminal transferase (Promega, Madison, Wis.). Hybridization was performed under medium stringency conditions: 40° C. in a solution containing 37.5% formamide 5× SSC (1× SSC is 0.15M sodium chloride, 0.015M sodium citrate), 1× Denhardt's solution (0.02% polyvinylpyrrolindone, 0.02% Ficoll, 0.02% bovine serum albumin), 7 mM Tris, and 25 µg/ml sonicated salmon sperm DNA. The filters were washed three times for 20 minutes at room temperature in a buffer containing 2× SSC/0.1% sodium dodecyl sulfate; two times for 20 minutes in a buffer containing 0.1× SSC/0.1% sodium dodecyl sulfate, and exposed at -70° C. to Kodak BioMax MS film in the presence of an intensifying screen.

Cosmid clones hybridizing with the probes were picked, streaked on plates, and screened a second time with the same probes to verify and isolate the individual positive colonies under the same conditions. Cosmid DNA from positive colonies was digested with BamHI and HindIII, run on an agarose gel, transferred to nitrocellulose, and probed with $^{32}$P-labelled BB426. A fragment of approximately 1.9 kb from clone #45a (COS4 library) that hybridized to the probe was subcloned into the BamHI/HindIII site of pEXJT3T7, an Okayama and Berg expression vector modified from pcEXV (Miller and Germain, 1986) to contain BstXI and other additional restriction sites as well as T3 and T7 promoters (Stratagene), and sequenced on both strands as described above. The construct of the human SNORF25 receptor in this vector is named pEXJT3T7-hSNORF25. Human SNORF25 was analyzed using the GCG software and was determined to contain the full-length sequence of human SNORF25, having 80% amino acid identity and 83% nucleotide identity to the rat receptor.

Oligonucleotide primers

The following is a list of primers and their associated sequences which were used in the cloning of these receptors:

| | | |
|---|---|---|
| JAB55: | 5'-TBDSYVYIGAYMGITAYVTKG-3' | (SEQ ID NO: 5) |
| TL1020: | 5'-GAIRSIARIGMRTAIAYIAKIGGRTT-3' | (SEQ ID NO: 6) |
| JAB1: | 5'-TTATGCTTCCGGCTCGTATGTTGTG-3' | (SEQ ID NO: 7) |
| JAB2: | 5'-ATGTGCTGCAAGGCGATTTAAGTTGGG-3' | (SEQ ID NO: 8) |
| JAB69: | 5'-TGGTCTGCTGGAATATGGAG-3' | (SEQ ID NO: 9) |
| JAB71: | 5'-CTTGGGTGAAACACAGCAAAGAAGG-3' | (SEQ ID NO: 10) |
| JAB72: | 5'-ATGGAACATGCAGGAGCCATGGTTGG-3' | (SEQ ID NO: 11) |
| JAB73: | 5'-AAGACAAAGAGGAGCACAGCTGGG-3' | (SEQ ID NO: 12) |
| JAB74: | 5'-GCTCAAGATTGCCTCTGTGCACAG-3' | (SEQ ID NO: 13) |
| JAB84: | 5'-ATCTATAAGCTTAGGCACTTGGAAACATCCATTCC-3' | (SEQ ID NO: 14) |
| JAB86: | 5'-ATCTATGGATCCTGTGAGAATCTGAGCTCAAGACCC-3' | (SEQ ID NO: 15) |
| BB426: | 5'-TTCACCTTAAATCTGGCCGTGGCTGATACCTTGAT- | (SEQ ID NO: 16) |

-continued

TGGCGTGGCTATTTCTGGGCTAG-3'

BB427:  5'-GCTGTGTTTCACCCAAGGTTTGTGCTGACCCTCTC-      (SEQ ID NO: 17)
        CTGTGCTGGCTTCTTCCCAGCTGTGC-3'

Isolation of other species homologs of SNORF25 receptor cDNA

A nucleic acid sequence encoding a SNORF25 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P-labeled oligonucleotide probe corresponding to a fragment of the human or rat SNORF25 receptors whose sequence is shown in FIGS. 1A–1B and 3A–3B to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1A–1B or 3A–3B. One may isolate a full-length SNORF25 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF25 which contain the additional sequence of SNORF25. These RACE PCR products may then be sequenced to determine the additional sequence. This new sequence is then used to design a forward PCR primer in the 5'UT and a reverse primer in the 3'UT. These primers are then used to amplify a full-length SNORF25 clone from cDNA.

Examples of other species include, but are not limited to, mouse, dog, monkey, hamster and guinea pig.

Host cells

A broad variety of host cells can be used to study heterologously expressed proteins. These cells include but are not limited to mammalian cell lines such as; Cos-7, CHO, LM(tk$^-$), HEK293, etc.; insect cell lines such as; Sf9, Sf21, etc.; amphibian cells such as Xenopus oocytes; assorted yeast strains; assorted bacterial cell strains; and others. Culture conditions for each of these cell types is specific and is known to those familiar with the art. The cells used to express SNORF25 receptor were Cos-7 and Chinese hamster ovary (CHO) cells.

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

CHO cells are grown on 150 mm plates in HAM's F-12 medium with supplements (10% bovine calf serum, 4 mM L-glutamine and 100 units/ml penicillin/100 µg/ml streptomycin) at 37° C., 5% $CO_2$. Stock plates of CHO cells are trypsinized and split 1:8 every 3–4 days.

Transient expression

DNA encoding proteins to be studied can be transiently expressed in a variety of mammalian, insect, amphibian, yeast, bacterial and other cell lines by several methods, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed. The electroporation method was used to transiently transfect various cell lines with SNORF25 cDNA.

A typical protocol for the electroporation method as applied to Cos-7 cells is described as follows. Cells to be used for transfection are split 24 hours prior to the transfection to provide flasks which are subconfluent at the time of transfection. The cells are harvested by trypsinization resuspended in their growth media and counted. $5 \times 10^6$ cells are suspended in 300 µl of DMEM and placed into an electroporation cuvette. 8 µg of receptor DNA plus 8 µg of any additional DNA needed (e.g. G protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µl of complete DMEM is added to each cuvette and the suspension transferred to a sterile tube. Complete medium is added to each tube to bring the final cell concentration to $1 \times 10^5$ cells/100 µl. The cells are then plated as needed depending upon the type of assay to be performed.

Stable expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the receptor of this invention, stable expression of a heterologous receptor protein is typically carried out in, mammalian cells including but not necessarily restricted to, CHO, HEK293, LM(tk–), etc.

In addition native cell lines that naturally carry and express the nucleic acid sequences for the receptor may be used without the need to engineer the receptor complement.

Membrane preparations

Cell membranes expressing the receptor protein according to this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 μg of viral DNA (BaculoGold) and 3 μg of DNA construct encoding a polypeptide may be co-transfected into 2×10$^6$ Spodoptera frugiperda insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Labeled ligand binding assays

Cells expressing the receptor according to this invention may be used to screen for ligands for said receptors, for example, by labeled ligand binding assays. Once a ligand is identified the same assays may be used to identify agonists or antagonists of the receptor that may be employed for a variety of therapeutic purposes.

In an embodiment, labeled ligands are placed in contact with either membrane preparations or intact cells expressing the receptor in multi-well microtiter plates, together with unlabeled compounds, and binding buffer. Binding reaction mixtures are incubated for times and temperatures determined to be optimal in separate equilibrium binding assays. The reaction is stopped by filtration through GF/B filters, using a cell harvester, or by directly measuring the bound ligand. If the ligand was labeled with a radioactive isotope such as $^3$H, $^{14}$C, 125I, $^{35}$S, $^{32}$P, $^{33}$P, etc., the bound ligand may be detected by using liquid scintillation counting, scintillation proximity, or any other method of detection for radioactive isotopes. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner agonist or antagonist compounds that bind to the receptor may be identified as they inhibit the binding of the labeled ligand to the membrane protein or intact cells expressing the receptor. Non-specific binding is defined as the amount of labeled ligand remaining after incubation of membrane protein in the presence of a high concentration (e.g., 100–1000×$K_D$) of unlabeled ligand. In equilibrium saturation binding assays membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Functional assays

Cells expressing the SNORF25 receptor DNA may be used to screen for ligands to SNORF25 receptor using functional assays. Once a ligand is identified the same assays may be used to identify agonists or antagonists of the SNORF25 receptor that may be employed for a variety of therapeutic purposes. It is well known to those in the art that the over-expression of a GPCR can result in the constitutive activation of intracellular signaling pathways. In the same manner, over-expression of the SNORF25 receptor in any cell line as described above, can result in the activation of the functional responses described below, and any of the assays herein described can be used to screen for both agonist and antagonist ligands of the SNORF25 receptor.

A wide spectrum of assays can be employed to screen for the presence of SNORF25 receptor ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) assay

The receptor-mediated stimulation or inhibition of cyclic AMP (cAMP) formation may be assayed in cells expressing the receptors. Cells are plated in 96-well plates or other vessels and preincubated in a buffer such as HEPES buffered saline (NaCl (150 mM), $CaCl_2$ (1 mM) , KCl (5 mM), glucose (10 mM)) supplemented with a phosphodiesterase inhibitor such as 5 mM theophylline, with or without protease inhibitor cocktail (For example, a typical inhibitor cocktail contains 2 μg/ml aprotinin, 0.5 mg/ml leupeptin, and 10 μg/ml phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

Arachidonic acid release assay

Cells expressing the receptor are seeded into 96 well plates or other vessels and grown for 3 days in medium with supplements. $^3$H-arachidonic acid (specific activity =0.75 μCi/ml) is delivered as a 100 μL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 μL. Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3H$ in a Trilux plate reader. Data are analyzed using nonlinear regression and statistical techniques available in the GraphPAD Prism package (San Diego, Calif.).

Inositol phosphate assay

SNORF25 receptor-mediated activation of the inositol phosphate (IP) second messenger pathways can be assessed by radiometric measurement of IP products.

In a 96 well microplate format assay, cells are plated at a density of 70,000 cells per well and allowed to incubate for 24 hours. The cells are then labeled with 0.5 μCi [$^3H$]-myo-inositol overnight at 37° C., 5% $CO_2$. Immediately before the assay, the medium is removed and replaced with 90 μL of PBS containing 10 mM LiCl. The plates are then incubated for 15 min at 37° C., 5% $CO_2$. Following the incubation, the cells are challenged with agonist (10 μl/well; 10× concentration) for 30 min at 37° C., 5% $CO_2$. The challenge is terminated by the addition of 100 μL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200–400 mesh, formate form). The filter plates are prepared adding 100 μL of Dowex AG1-X8 suspension (50% v/v, water: resin) to each well. The filter plates are placed on a vacuum manifold to wash or elute the resin bed. Each well is first washed 2 times with 200 μl of 5 mM myo-inositol. Total [$^3H$]inositol phosphates are eluted with 75 μl of 1.2M ammonium formate/0.1M formic acid solution into 96-well plates. 200 μL of scintillation cocktail is added to each well, and the radioactivity is determined by liquid scintillation counting.

Intracellular calcium mobilization assays

The intracellular free calcium concentration may be measured by microspectrofluorimetry using the fluorescent indicator dye Fura-2/AM (Bush et al, 1991). Cells expressing the receptor are seeded onto a 35 mm culture dish containing a glass coverslip insert and allowed to adhere overnight. Cells are then washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 80,000–150,000 cells per well and allowed to incubate for 48 hr at 5% $CO_2$, 37° C. The growth medium is aspirated and 100 μl of loading medium containing fluo-3 dye is added to each well. The loading medium contains: Hank's BSS (without phenol red) (Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma)(prepared fresh). The cells are allowed to incubate for about 1 hour at 5% $CO_2$, 37° C.

During the dye loading incubation the compound plate is prepared. The compounds are diluted in wash buffer (Hank's BSS (without phenol red), 20 mM HEPES, 2.5 mM probenecid) to a 4× final concentration and aliquoted into a clear v-bottom plate (Nunc). Following the incubation the cells are washed to remove the excess dye. A Denley plate washer is used to gently wash the cells 4 times and leave a 100 μl final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

GTPγS functional assay

Membranes from cells expressing the receptor are suspended in assay buffer (e.g., 50 mM Tris, 100 mM NaCl, 5 mM $MgCl_2$, 10 μM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration=100 μM). Final membrane protein concentration≈90 μg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}S$ in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

Microphysiometric assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and illdefined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 µl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 µM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP kinase assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell proliferation assay

Receptor activation of the receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. Twenty-four hours later, the cells are incubated with $^3$H-thymidine at specific activities ranging from 1 to 10 µCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the receptor, which can be detected by methods such as, but not limited to, florescence intensity, enzymatic activity, immunoreactivity, DNA hybridization, polymerase chain reaction, etc.

Promiscuous second messenger assays

It is not possible to predict, a priori and based solely upon the GPCR sequence, which of the cell's many different signaling pathways any given receptor will naturally use. It is possible, however, to coax receptors of different functional classes to signal through a pre-selected pathway through the use of promiscuous $G_\alpha$ subunits. For example, by providing a cell based receptor assay system with an endogenously supplied promiscuous $G_f$ subunit such as $G_{\alpha 15}$ or $G_{\alpha 16}$ or a chimeric $G_\alpha$ subunit such as $G_{\alpha q z}$, a GPCR, which might normally prefer to couple through a specific signaling pathway (e.g., $G_s$, $G_i$, $G_q$, $G_o$, etc.), can be made to couple through the pathway defined by the promiscuous $G_\alpha$ subunit and upon agonist activation produce the second messenger associated with that subunit's pathway. In the case of $G_{\alpha 15}$, $G_{\alpha 16}$ and/or $G_{\alpha q z}$ this would involve activation of the $G_q$ pathway and production of the second messenger $IP_3$. Through the use of similar strategies and tools, it is possible to bias receptor signaling through pathways producing other second messengers such as $Ca^{++}$, cAMP, and $K^+$ currents, for example (Milligan, 1999).

It follows that the promiscuous interaction of the exogenously supplied $G_\alpha$ subunit with the receptor alleviates the need to carry out a different assay for each possible signaling pathway and increases the chances of detecting a functional signal upon receptor activation.

Methods for recording currents in Xenopus oocytes

Oocytes are harvested from *Xenopus laevis* and injected with mRNA transcripts as previously described (Quick and Lester, 1994; Smith et al.,1997). The test receptor of this invention and Gα subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous Gα subunits mRNA in order to observe coupling to $Ca^{++}$ activated $Cl^-$ currents. Dual electrode voltage clamp (Axon Instruments Inc.) is performed using 3M KCl-filled glass microelectrodes having resistances of 1–2 MOhm. Unless otherwise specified, oocytes are voltage clamped at a holding potential of −80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μl glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying $K^+$ (GIRK) channels 1, 2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying a test compound in ND96 solution to oocytes previously injected with mRNA for the SNORF25 receptor and observing inward currents at a holding potential of approximately −80 mV. The appearance of currents that reverse at −25 mV and display other properties of the $Ca^{++}$-activated $Cl^-$ channel is indicative of receptor-activation of PLC and release of $IP_3$ and intracellular $Ca^{++}$. Such activity is exhibited by GPCRs that couple to $G_q$ or $G_{11}$.

Involvement of the $G_{i/o}$ class of G-proteins in GPCR-stimulated $Ca^{++}$-activated $Cl^-$ currents is evaluated using PTX, a toxin which inactivates $G_{i/o}$ G-proteins. Oocytes are injected with 25 ng PTX/oocyte and modulation of $Ca^{++}$-activated $Cl^-$ currents by SNORF25 receptor is evaluated 2–5 h subsequently.

Elevation of intracellular cAMP can be monitored in oocytes by expression of the cystic fibrosis transmembrane conductance regulator (CFTR) whose $Cl^-$-selective pore opens in response to phosphorylation by protein kinase A (Riordan, 1993). In order to prepare RNA transcripts for expression in oocytes, a template was created by PCR using 5' and 3' primers derived from the published sequence of the CFTR gene (Riordan, 1993). The 5' primer included the sequence coding for T7 polymerase so that transcripts could be generated directly from the PCR products without cloning. Oocytes were injected with 10 ng of CFTR mRNA in addition to 10–15 ng mRNA for SNORF25. Electrophysiological recordings were made in ND96 solution after a 2–3 day incubation at 18° C. Currents are recorded under dual electrode voltage clamp (Axon Instruments Inc.) with 3M KCl-filled glass microelectrodes having resistances of 1–2 Mohm. Unless otherwise specified, oocytes are voltage clamped at a holding potential of −80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μl glass capillary tube fixed at a distance of 0.5 mm from the oocyte, or by switching from a series of gravity fed perfusion lines.

Activation of G-protein $G_i$ and $G_o$ can be monitored by measuring the activity of inwardly rectifying $K^+$ (potassium) channels (GIRKs). Activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the GIRK subunits are tested for test compound responsivity by measuring $K^+$ currents in elevated $K^+$ solution containing 49 mM $K^+$.

Localization of mRNA coding for human and rat SNORF25.

Methods: Quantitative RT-PCR using a fluorogenic probe with real time detection.

Quantitative RT-PCR using fluorogenic probes and a panel of mRNA extracted from human and rat tissue was used to characterize the localization of SNORF25 rat and human RNA.

This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein) and JOE (6 carboxy-4.5-dichloro-2,7-dimethoxyfluorescein) were the two reporters that were utilized and TAMRA (6-carboxy-4,7,2,7'-tetramethylrhodamine) was the quencher. As amplification progresses, the labelled oligonucleotide probe hybridizes to the gene sequence between the two oligonucleotides used for amplification. The nuclease activity of Taq, or rTth thermostable DNA polymerases is utilized to cleave the labelled probe. This separates the quencher from the reporter and generates a fluorescent signal that is directly proportional to the amount of amplicon generated. This labelled probe confers a high degree of specificity. Non-specific amplification is not detected as the labelled probe does not hybridize. All experiments were conducted in a PE7700 Sequence Detection System (Perkin Elmer, Foster City, Calif.).

Quantitative RT-PCR

For the detection of RNA encoding SNORF25, quantitative RT-PCR was performed on mRNA extracted from tissue. Reverse transcription and PCR reactions were carried out in 50 μl volumes using rTth thermostable DNA polymerase (Perkin Elmer). Primers with the following sequences were used:

SNORF 25 human:

Forward primer:
SNORF25H-765F
5'-CCTCTACCTAGTGCTGGAACGG-3'  (SEQ ID NO: 18)

Reverse primer
SNORF25H-868R
5'-GCTGCAGTCGCACCTCCT-3'  (SEQ ID NO: 19)

Fluorogenic oligonucleotide probe:
SNORF25H-814T
5' (6-FAM)-*TCCCTGCTCAACCCACTCATCTATGCCTATT*-(TAMRA) 3'  (SEQ ID NO: 20)

SNORF25 rat forward primer
SNORF25R-231F
5'-GTGTAGCCTTCGGATGGCA-3'  (SEQ ID NO: 21)

reverse primer
SNORF25R-329R
5'-GGCTGCTTAATGGCCAGGTAC-3'  (SEQ ID NO: 22)

Fluorogenic oligonucleotide probe:
SNORF2SR-278T
5' (6-FAM)-TCCTCACGGTCATGCTGATTGCCTTT-(TAMRA)3'  (SEQ ID NO: 23)

Using these primer pairs, amplicon length is 104 bp for human SNORF25 and 99 bp for rat SNORF25. Each RT-PCR reaction contained 50 ng mRNA. Oligonuceotide concentrations were: 500 nM of forward and reverse primers, and 200 nM of fluorogenic probe. Concentrations of reagents in each reaction were: 300 μM each of dGTP; dATP; dCTP; 600 μM UTP; 3.0 mM Mn(OAc)2; 50 mM Bicine; 115 mM potassium acetate, 8% glycerol, 5 units rTth thermostable DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotide primers) were obtained from Perkin Elmer (Foster City, Calif.). Reactions were carried using the following thermal cycler profile: 50° C. 2 min., 60° C. 30 min., 95° C. 5 min., followed by 40 cycles of: 94° C., 20 sec., 62° C. 1 min.

Positive controls for PCR reactions consisted of amplification of the target sequence from a plasmid construct. Standard curves for quantitation were constructed using the human SNORF25 gene in a plasmid vector or RNA extracted from pancreas as a template for amplification. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of mRNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted to a standard curve to obtain relative quantities of SNORF25 mRNA expression.

RESULTS AND DISCUSSION

Cloning of the full-length sequence of SNORF25

Genomic DNA and cDNA prepared from several tissues (including GH1 cells and Rin14b cells) was subjected to MOPAC PCR with two degenerate primers designed based on the third transmembrane domain of the members of the galanin, somatostatin, and opioid receptor families and the seventh transmembrane domain of members of the galanin receptor family. Three products from this reaction were found to be the same clone in either orientation (forward or reverse), which was a novel sequence not found in the Genbank, SwissProtPlus, GSS, EST, or STS databases. It contained significant homology to other known G protein-coupled receptors (~29% identity to the known receptors dopamine D1, beta-adrenergic 2b and 5-HT$_{1F}$; 34% identity to 5-HT$_{4L}$ receptor). This receptor sequence was later named SNORF25, and was used to design primers for 5' and 3' Rapid Amplification of cDNA Ends (RACE), as described in the Methods section above. The 5' RACE reaction yielded sequence information through the first transmembrane domain and a putative in-frame initiating methionine-coding sequence surrounded by a kozak consensus sequence (ACCATGG).

The 3' RACE reaction yielded a 600 bp band by agarose gel electrophoresis. This band was subcloned into the TA cloning kit, and isolated colonies were sequenced. The sequence of these products revealed the presence of an in-frame stop codon downstream from the region coding for the seventh transmembrane domain. The entire size of the coding sequence of SNORF25 was determined to be 1005 bp, coding for a protein of 335 amino acids. Two primers, JAB86 and JAB84, were used to amplify the entire coding sequence from Rin14b cell line cDNA and rat genomic DNA using the Expand Long PCR system. The primers for this reaction were specific to the 5' and 3' untranslated regions of SNORF25 with BamHI and HindIII restriction sites incorporated into the 5' ends of the 5' and 3' primers, respectively. When the products of these reactions were subcloned into pcDNA3.1(−) and sequenced, the sequence of the Rin14b clone and the genomic clone were found to be identical, and the vector construct containing rat SNORF25 was named pcDNA3.1-rSNORF25.

Hydophobicity (Kyte-Doolittle) analysis of the amino acid sequence of the full-length clone indicates the presence of seven hydrophobic regions, which is consistent with the seven transmembrane domains of a G protein-coupled receptor. The seven expected transmembrane domains are indicated in FIG. 4. A comparison of nucleotide and peptide sequences of rat SNORF25 with sequences contained in the Genbank, EMBL, and SwissProtPlus databases reveals that the amino acid sequence of this receptor is most related to histamine, adenosine, serotonin, beta adrenergic, and dopamine receptor families, displaying between 25–30% overall amino acid identity with these receptors. The N- and C-termini are relatively short, much like the adenosine receptor family. However, transmembrane domain analysis indicates that this receptor shares a significant degree of identity to other GPCRs in its transmembrane domains. A comparison of all of the transmembrane domains of SNORF25 simultaneously with a comprehensive list of GPCR transmembrane domains would suggest that the transmembrane domains of SNORF25 have the highest degree of identity with the beta adrenergic receptors 1 and 2 of 31% and 32%, respectively, as well as 5-HT$_7$ and 5-hT$_{5B}$ receptors of 32% and 36.6%, respectively. When transmembrane domains are analyzed individually by a FASTA search, SNORF25 exhibits considerable similarity to the transmembrane domains of a variety of known G protein-coupled receptors.

Figure 2A:
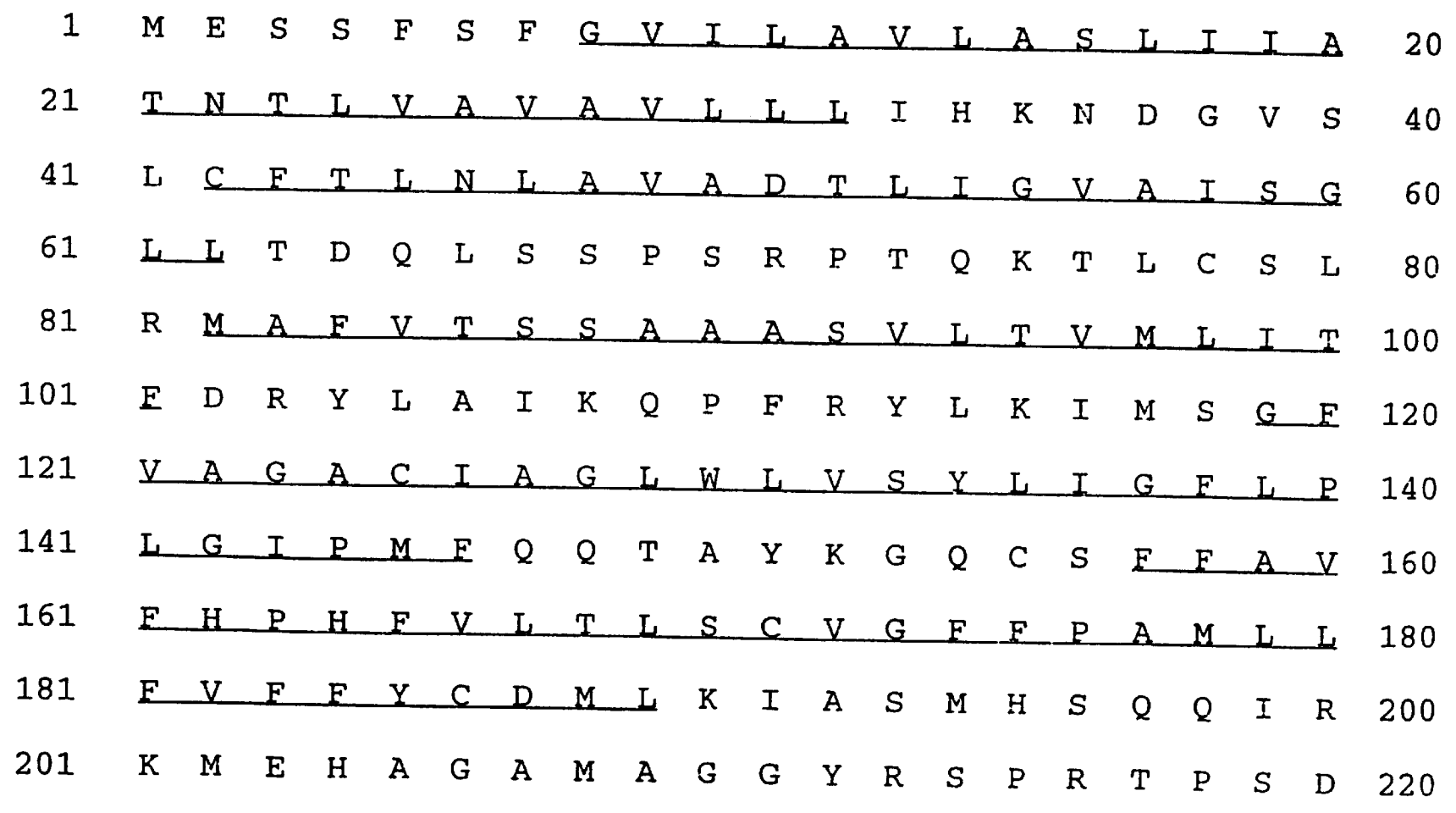
Figure 2B:
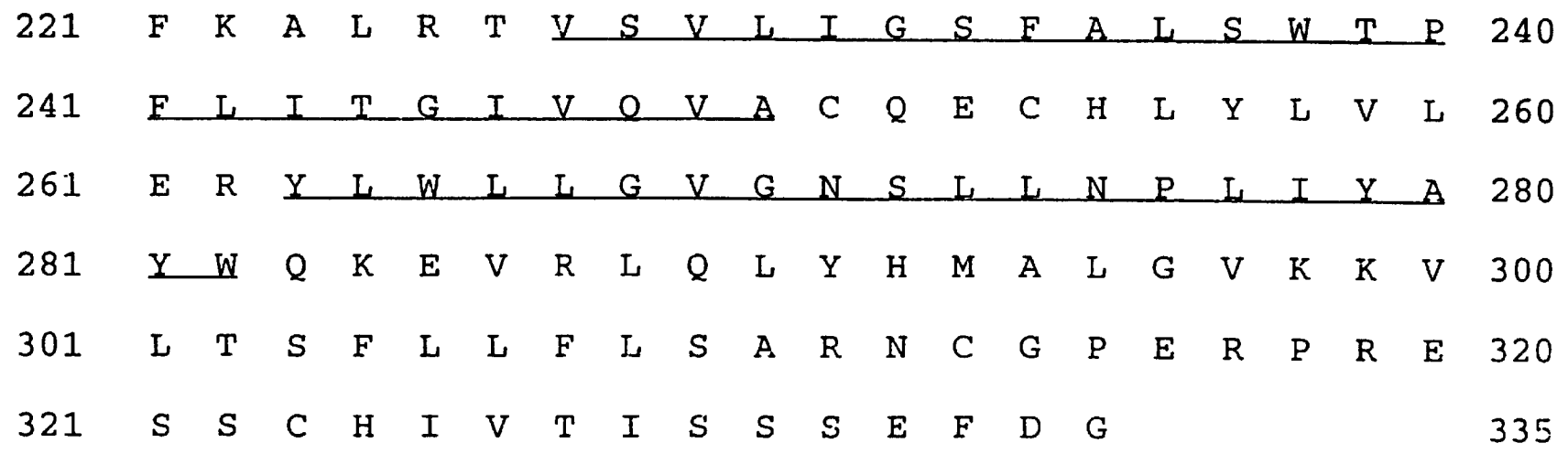

In order to clone the human homolog of SNORF25, a human genomic cosmid library was screened at medium stringency with labelled oligonucleotide probes designed based on the second and fifth transmembrane domains of rat SNORF25. Out of roughly 225,000 colonies screened, two colonies hybridized to the probes. After isolation and analysis of each colony, these two clones were determined to be identical cosmid clones containing the human homolog of SNORF25. Southern blot analysis of several restriction digests of this cosmid and subsequent sequencing of positive bands indicated that a BamHI/HindIII digest of this cosmid yielded a 1.9 kb fragment containing the full-length coding sequence of this human clone. The construct of the human receptor subcloned into the BamHI/HindIII site of the pEXJT3T7 vector is named pEXJT3T7-hSNORF25. Human SNORF25 exhibits an 80% DNA identity and 83% amino acid identity to rat SNORF25. Like the rat receptor, the protein-coding region of human SNORF25 is 1005 nucleotides (FIGS. 1A–1B), coding for a protein of 335 amino acids (FIGS. 2A–2B). The DNA and amino acid sequences of rat SNORF25 are shown in FIGS. 3A–3B and 4A–4B, respectively.

A search of the GenEMBL, SwissProtPlus, EST, STS and GSS databases confirmed that human SNORF25 is also a unique novel sequence. Other than its identity with rat SNORF25, it shares 28–30% overall identity with adenosine 2a, 5-HT$_{4L}$, 5-HT$_{4S}$, 5-H$_{T6}$, and 5-HT$_7$, dopamine D$_1$ and D$_5$, and somatostatin 5 receptors. It also shares 25–26% identity with adenosine A1, histamine H1 and 2, beta adrenergic 1, and somatostatin 2 and 3 receptors. A comparison of all of the transmembrane domains of human SNORF25 simultaneously with a comprehensive list of GPCR transmembrane domains would suggest that the transmembrane domains of human SNORF25 have the highest degree of identity with the beta 1 and 2 adrenergic receptors (29% and 32%, respectively) and 5-HT$_4$. Individual transmembrane domains of human SNORF25 share significant identity with transmembrane domains from several other G protein-coupled receptors.

Both rat and human SNORF25 have several potential protein kinase C (PKC) phosphorylation motifs throughout their amino acid sequences. For both receptors, threonine 73, serine 79, and serine 309 are potential PKC phosphorylation sites. The human receptor has an additional putative PKC phosphorylation site at serine 214, which is a proline in rat SNORF25. Both receptors share a potential casein kinase II (CKII) phosphorylation site at serine 329. The human SNORF25 also contains two more potential CKII phosphorylation sites, threonine 217 and serine 331, that are not present in the rat receptor. Conversely, rat SNORF25 contains a potential tyrosine phosphorylation site at tyrosine 323, which is not present in the human receptor.

cAMP response of SNORF25-transfected cells

Figure 5:
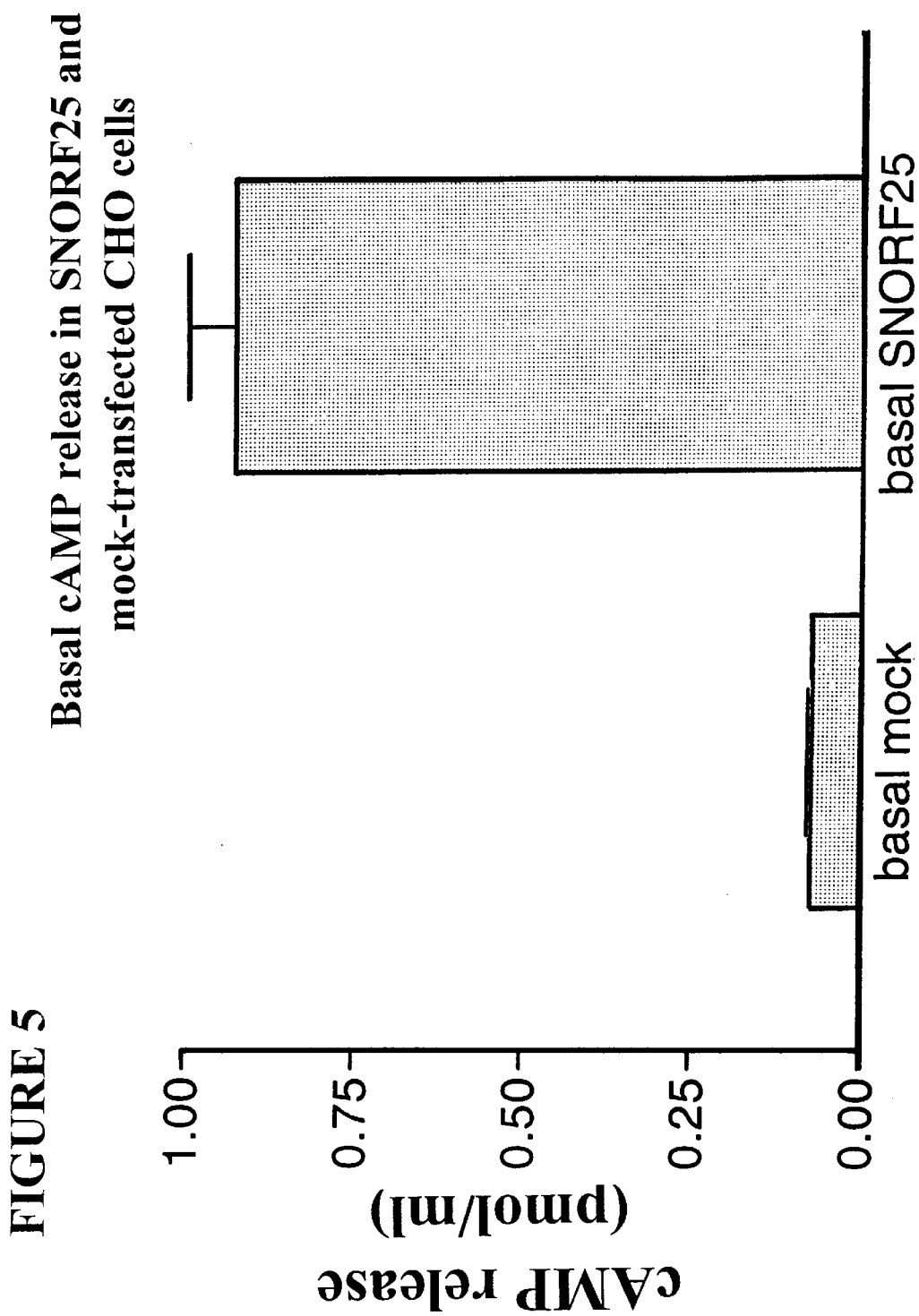

The expression vector (pcDNA) containing the SNORF25 cDNA was transfected by electroporation method into CHO cells. After plating, the transfectants were challenged with a ligand library that included, among other things, several of the traditional neurotransmitters such as histamine, adenosine, serotonin, norepinephrine, and dopamine, based on homology of SNORF25 to the receptors of these ligands (see above), and tested for their ability to stimulate cAMP or IP release above mock-transfected cells. Interestingly, the basal cAMP levels of SNORF25-transfected cells were significantly higher (>10-fold) than mock-transfected cells (FIG. 5). This observation suggested that SNORF25 receptor may functionally be coupled to a cAMP stimulatory pathway. Among the ligands tested, only all-trans retinoic acid (ATRA) produced a significant increase in cAMP but not IP release in SNORF25-transfected cells, without affecting these parameters in mock-transfected CHO cells. The response produced at 10 $\mu$M concentration of ATRA (2- to 5-fold above basal) was comparable to that produced by forskolin, a potent direct stimulator of adenylyl cyclase (FIG. 6) (n=3).

Figure 6:
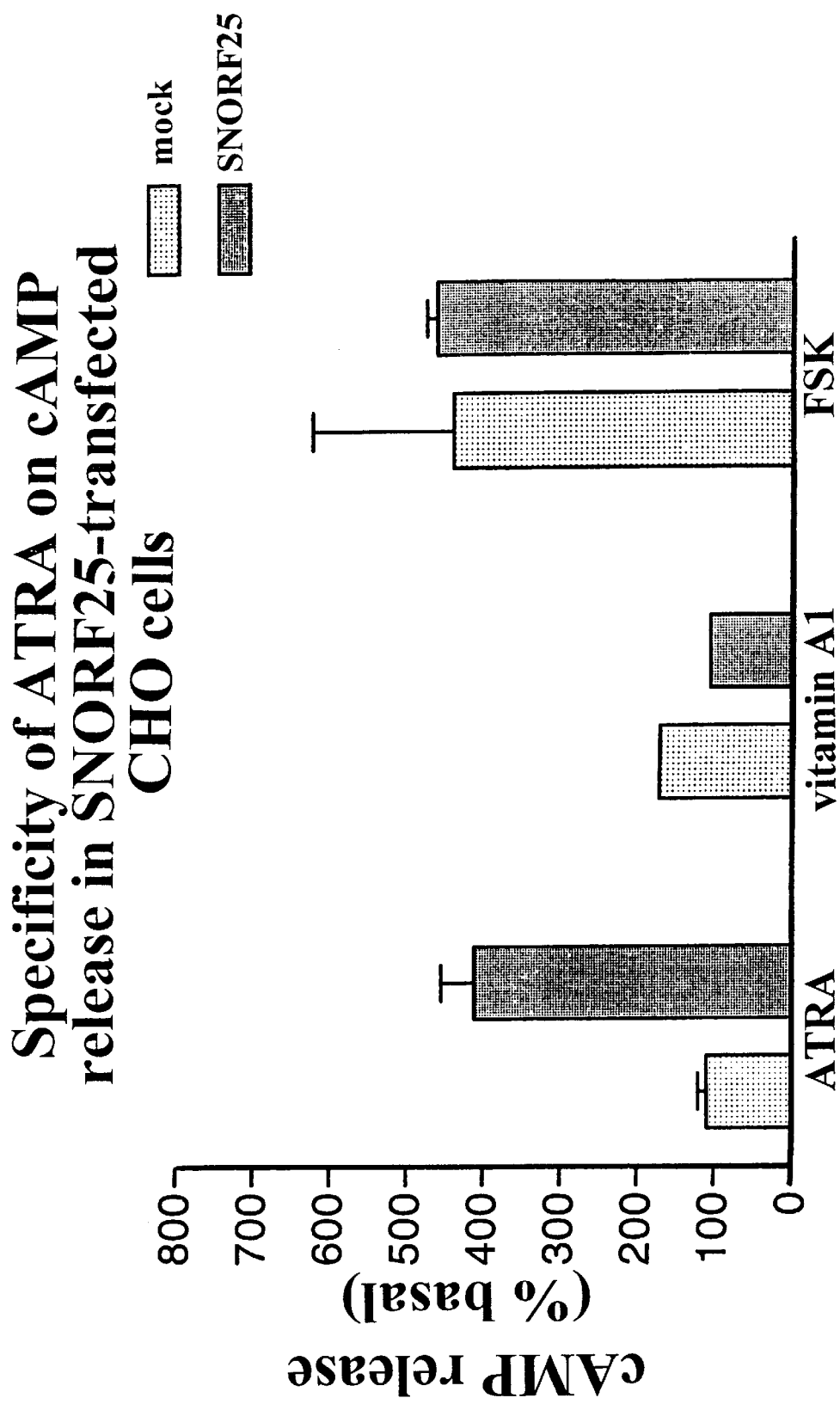

Responses to forskolin in both mock- and SNORF25-transfected Cos-7 cells were almost identical (FIG. 6), suggesting that the enhanced maximal response to ATRA observed in SNORF25-expressing cells, as compared to mock DNA-transfected cells, was not due to a change in cell density or in the intrinsic properties of the cells. All-trans retinol (vitamin A$_1$), a close analogue of ATRA failed to produce an increase in cAMP at 10 $\mu$M (FIG. 6).

Figure 7:
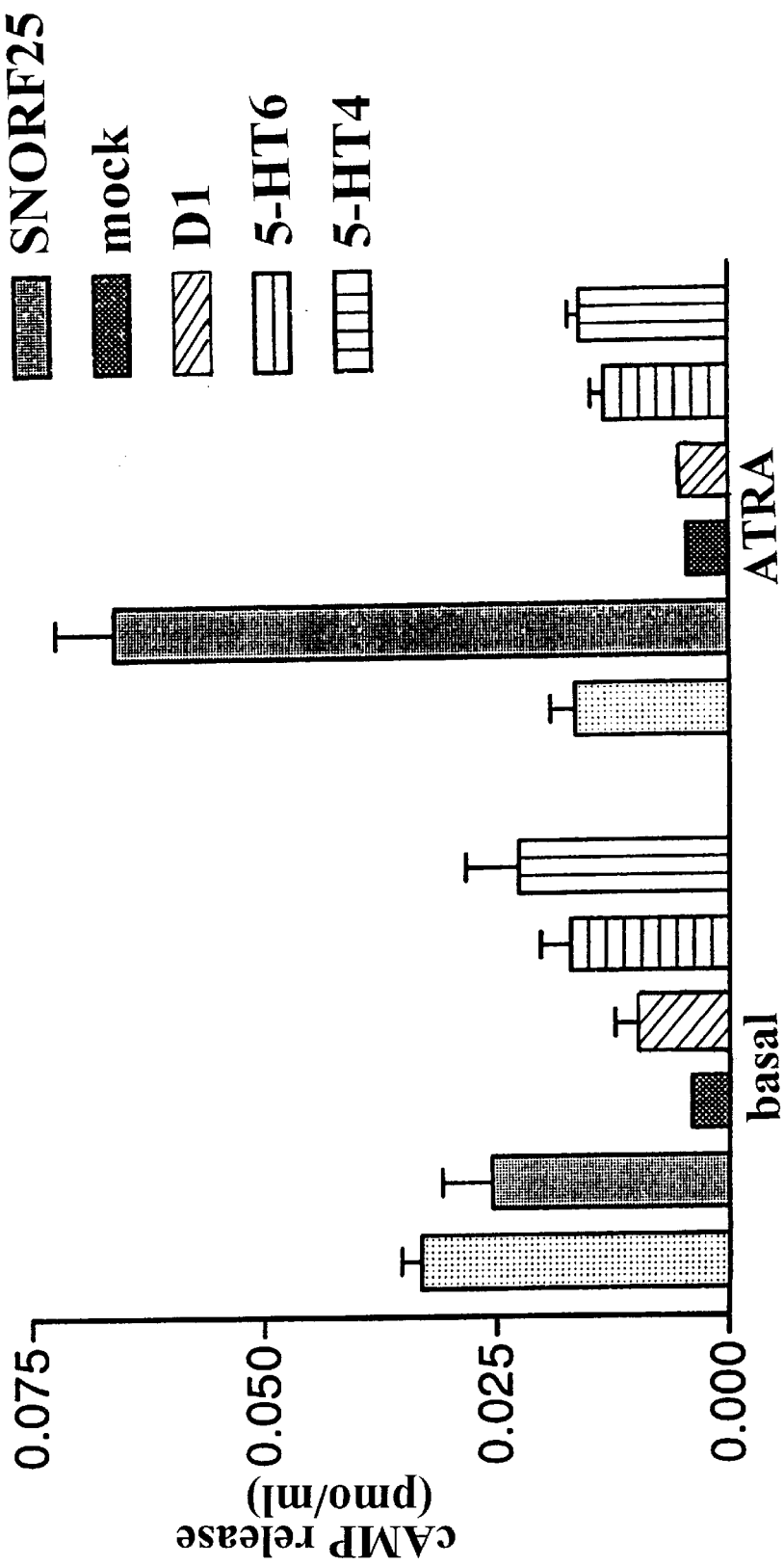

Subsequent experiments demonstrated that the ATRA-induced increase in cAMP formation was independent of host cell as it was observed also in Cos-7 cells (n=3) (FIG. 7). All-trans-retinoic acid produced no response in Cos-7 cells transfected with other known cyclase-stimulatory receptors including dopamine D1, D5, serotonin 5-HT4 and 5-HT6 receptors, indicating that the response observed to ATRA is specific to SNORF25-transfected cells (FIG. 7).

The cAMP response to ATRA in Cos-7 cells was concentration-dependent with EC$_{50}$ values ranging from approximately 0.2 to 1 $\mu$M and E$_{max}$ of approximately 200–300% (FIG. 8).

Activation of calcium-activated Cl$^-$ currents in SNORF25 expressing Xenopus oocytes Elevation of intracellular cAMP can be monitored in oocytes by expression of the cystic fibrosis transmembrane conductance regulator (CFTR) whose Cl$^-$-selective pore opens in response to phosphorylation by protein kinase A (Riordan, 1993). The activity of SNORF25 was therefore tested in oocytes co-injected with mRNA encoding SNORF25 and mRNA encoding CFTR. In 17 out of 39 of these ooctyes an inward Cl$^-$ current (105±20 nA) was measured in response to the application of 10 $\mu$M all-trans-retinoic acid (See FIGS. 9A–9C and 10).

This response was specific to the expression of SNORF25 since no such current was observed in other oocytes injected with only mRNA encoding the CFTR channel. Similar currents were observed in oocytes injected with the β2-adrenergic receptor (B2AR) (See FIG. 9C), although the currents generated by SNORF25-expressing oocytes were generally 2–3 fold slower and smaller. All-trans-retinoic acid did not stimulate Cl⁻ currents in oocytes lacking CFTR, indicating that the Gq-mediated phospholipase C pathway was not activated. Responses also were not evoked in ooctyes expressing chimeric G-proteins which are able to couple Gi and Go coupled GPCRs to the phospholipase C pathway. Taken together, these observations support the hypothesis that SNORF25 encodes a GPCR which binds all-trans-retinoic acid and stimulates the production of cAMP, presumably via activation of Gs.

In other systems, all-trans-retinoic acid stimulates one of several nuclear receptors (see background). This results in the enhancement of transcription of one or more genes. SNORF25 expression in oocytes could result in the expression of a nuclear receptor for all-trans-retinoic acid, not normally present in uninjected oocytes, that when stimulated produces an elevation of cAMP. If this were the case, then retinoic acid would not necessarily bind the SNORF25 receptor, but would act on a previously know or novel nuclear receptor for retinoic acid. This indirect mechanism of action of retinoic acid may explain why the ligand failed to elicit a CFTR response in 3 out of 6 batches of oocytes (17 of 39 oocytes), and why the kinetics of CFTR activation were 2–3 times slower than those observed under conditions where responses were evoked by activation of well-characterized GPCRs such as the B2 adrenergic receptor (FIG. 9C). Nevertheless, the delay for activation of CFTR by retinoic acid was on the order of 10 seconds, and the activation of nuclear receptors is typically in the range of several minutes to hours. Thus, while we cannot rule out an indirect mechanism of action of retinoic acid, the relatively rapid onset of the response in SNORF25-expressing oocytes suggests that such a mechanism is unlikely.

Detection of mRNA coding for human SNORF25:

mRNA was isolated from multiple tissues (listed in Table 1) and assayed as described.

Quantitative RT-PCR using a fluorgenic probe demonstrated expression of mRNA encoding human SNORF25 in most tissues assayed (Table 1). Highest levels of human SNORF25 mRNA are found in the pancreas, stomach, small intestine and fetal liver, with lower levels detected elsewhere. Most nervous system structures showed little expression of SNORF25 mRNA as compared to peripheral organs.

The highest levels of SNORF25 expression are found in the pancreas. The pancreas secretes a variety of broadly active substances (including insulin), indicating that SNORF25 may play a role in regulating multiple metabolic functions, potentially via endocrine mechanisms. SNORF25 expression in the pancreas is not surprising as SNORF25 is also expressed in a rat insulinoma cell line. This finding as well as the detection of SNORF25 mRNA in liver indicate a possible role in the regulation of glucose levels and possibly diabetes.

Other organs with high levels of SNORF25 mRNA are stomach and small intestine. The distribution to these structures is consistent with functions relating to gastrointestinal motility or absorption. It is not known at this time if SNORF25 mRNA is localized to smooth muscle or to mucosal/submucosal layers.

Although detected in very low levels, the presence of SNORF25 mRNA in multiple regions of the CNS including the thalamus and hippocampal formation (where levels are highest in the CNS) and other functionally diverse areas, indicate a diffuse regulatory function or regional functionality for this receptor.

Human SNORF25 mRNA appears to be developmentally regulated. In fetal liver, levels of mRNA approach those measured in adult pancreas (83%). However in adult tissue, this drops to less than 1% of the amount found in the pancreas. The profound change of SNORF25 mRNA during development implies a role in the maturation of the liver, or a role in the regulation of glucose demands/levels during development. The time course of this increase has not been examined and would be important in understanding the function of this receptor.

In summary, the distribution of SNORF25 receptor mRNA implies broad regulatory functions that involves multiple organ systems, endocrine mechanisms, as well as the central nervous system.

Detection of mRNA coding for rat SNORF25

Unlike the restricted distribution of human SNORF25 mRNA, the distribution of SNORF25 mRNA in the rat is widespread. One striking difference in the distribution between rat and human is the high levels of SNORF25 mRNA detected in the rat central nervous system. In the human, the highest concentrations of SNORF25 mRNA are found in the pancreas, with very low levels found in CNS structures. In the rat the highest levels of SNORF25 mRNA are found in the hippocampal formation, closely followed by levels detected in the cerebral cortex, cerebellum, hypothalamus, choroid plexus and medulla. SNORF25 mRNA is also detected in both dorsal root and trigeminal ganglia. Although SNORF25 mRNA is detected in rat pancreas and other peripheral organs, it is present there in much lower levels than in the CNS.

Rat SNORF25 was detected in most tissues assayed. In addition to the pancreas it is expressed in appreciable amounts in lung, colon, duodenum, ovary, kidney and the adrenal glands. It was detected in other tissues in decreasing amounts as shown in Table 2.

In summary, the broad distribution of rat SNORF25 receptor mRNA implies broad regulatory functions that involve multiple organ systems, endocrine mechanisms as well as the central nervous system. The difference in the distribution pattern seen between human and rat suggests a broader, and potentially different role for this receptor in the rat as compared to human.

TABLE 1

Distribution of mRNA coding for human SNORF25 receptors using qRT-PCR
mRNA encoding SNORF25h is expressed as % of highest expressing tissue.

| Region | qRT-PCR % of max | Potential applications |
|---|---|---|
| heart | 0.31 | cardiovascular indications |
| kidney | 0.62 | hypertension, electrolyte balance |
| liver | 0.18 | diabetes |
| lung | 0.32 | respiratory disorders, asthma |
| pancreas | 100 | diabetes, endocrine disorders |
| pituitary | 0.03 | endocrine/neuroendocrine regulation |
| placenta | 0.42 | gestational abnormalities |
| small intestine | 4.63 | gastrointestinal disorders |
| spleen | 1.50 | immune disorders |
| stomach | 12.60 | gastrointestinal disorders |
| striated muscle | 0.32 | musculoskeletal disorders |
| amygdala | 0.18 | depression, phobias, anxiety, mood disorders |
| caudate-putamen | 0.17 | modulation of dopaminergic function |
| cerebellum | 0.06 | motor coordination |
| cerebral cortex | 0.01 | sensory and motor integration, cognition |
| hippocampus | 0.27 | cognition/memory |

TABLE 1-continued

Distribution of mRNA coding for human SNORF25 receptors using qRT-PCR
mRNA encoding SNORF25h is expressed as % of highest expressing tissue.

| Region | qRT-PCR % of max | Potential applications |
|---|---|---|
| spinal cord | 0.00 | analgesia, sensory modulation and transmission |
| substantia nigra | 0.05 | modulation of dopaminergic function. modulation of motor coordination. |
| thalamus | 0.60 | sensory integration |
| fetal brain | 0.14 | developmental disorders |
| fetal lung | 0.04 | developmental disorders |
| fetal kidney | 0.90 | developmental disorders |
| fetal liver | 82.63 | developmental disorders |

TABLE 2

Distribution of mRNA coding for rat SNORF25 receptors using qRT-PCR
mRNA encoding SNORF25r is expressed as % of highest expressing tissue.

| Tissue | qRT-PCR % of max | Potential applications |
|---|---|---|
| adipose tissue | 9.08 | metabolic disorders |
| adrenal cortex | 8.78 | regulation of steroid hormones |
| adrenal medulla | 16.34 | regulation of epinephrine release |
| colon | 24.15 | gastrointestinal disorders |
| duodenum | 18.89 | gastrointestinal disorders |
| heart | 11.98 | cardiovascular indications |
| kidney | 15.86 | electrolyte balance, hypertension |
| liver | trace | diabetes |
| lung | 32.57 | respiratory disorders, asthma |
| ovary | 17.74 | reproductive function |
| pancreas | 30.45 | diabetes, endocrine disorders |
| spleen | not detected | immune disorders |
| stomach | 3.44 | gastrointestinal disorders |
| striated muscle | 1.04 | musculoskeletal disorders |
| testes | 5.10 | reproductive function |
| urinary bladder | 7.87 | urinary incontinence |
| vas deferens | 7.16 | reproductive function |
| celiac plexus | 17.82 | modulation of autonomic innervation |
| cerebellum | 84.14 | motor coordination |
| cerebral cortex | 83.54 | Sensory and motor integration, cognition |
| choroid plexus | 66.59 | regulation of cerebrospinal fluid |
| dorsal root ganglia | 38.14 | sensory transmission |
| hippocampus | 100 | cognition/memory |
| hypothalamus | 67.19 | appetite/obesity neuroendocrine regulation |
| medulla | 52.66 | analgesia, motor coordination |
| olfactory bulb | 6.66 | olfaction |
| pineal gland | 41.16 | regulation of melatonin release |
| spinal cord | 31.72 | analgesia, sensory modulation and transmission |
| trigeminal ganglia | 42.98 | sensory transmission |

REFERENCES

Bowman, W. C. and Rand, M. J., eds., "The eye and drugs affecting ocular function", In: *Textbook of Pharmacology.* Second Edition, London: Blackwell Scientific Publications. p.29.22–29.27 (1980).

Bradford, M. M., "A rapid and sensitive method for the quantitation of microgram quantities of protein utilizing the principle of protein-dye binding", Anal. Biochem. 72: 248–254 (1976).

Breitman, T., et al., "Induction of differentiation of human promyelocytic leukemia cell line (HL-60) by retinoic acid", *Proc. Natl. Ada. Sci.* 77: 2936–2940 (1980).

Burns, C. C., et al., "Indentification and deletion of sequences required for feline leukemia virus RNA packaging and construction of a high-titer feline leukemia virus packaging cell line", *Virology* 222 (1): 14–20 (1996).

Bush, et al., "Nerve growth factor potentiates bradykinin-induced calcium influx and release in PC12 cells", *J. Neurochem.* 57: 562–574 (1991).

Chertow, B. S., et al., "Cellular mechanisms of insulin release: effects of retinoids on rat islet cell-to-cell adhesion, reaggregation, and insulin release", *Diabetes* 32: 568–574 (1983).

Chertow, B. S., et al, "Effects of vitamin A deficiency and repletion on rat insulin secretion in vivo and in vitro from isolated islets", *J. Clin. Invest.* 79: 163–169(1987)

Chertow, B. S., et al., "Cytoplasmic retinoid-binding proteins and retinoid effects on insulin release in RINm5F -cells", *Diabetes* 38: 1544–1548 (1989).

Chu, Y. Y., et al., "Characterization of the rat A2a adenosine receptor gene", *DNA Cell Biol.* 15(4): 329–337 (1996).

Chytil, F., "Retinoids in lung development", *FASEB J.* 10(9): 986–992 (1996).

Connor, M. J. and Sidell, N., "Retinoic acid synthesis in normal and Alzheimer diseased brain and human neural cells", *Mol. Chem. Neurophathol.* 30(3): 239–252 (1997).

Dascal, N., et al., "Atrial G protein-activated $K^+$ channel: expression cloning and molecular properties", *Proc. Natl. Acad. Sci. USA* 90:10235–10239 (1993).

El-Matwally, T. H. and T. E. Adrian (1999) Optimization of treatment conditions for studying the anticancer effects of retinoids using pancreatic adenocarcinoma as a model. *Biochem. Biophy. Res. Commun.* 257(2): 596–603.

Fong, T. M., et al., "Mutational analysis of neurokinin receptor function" *Can. J. Physio. Pharmacol.* 73(7): 860–865 (1995).

Goodman, A. B., "Three independent lines of evidence suggest retinoids as causal to schizophrenia", *PNAS* 95(13): 7240–7244 (1998).

Gattardis, M. M., et al., "The efficacy of 9-c is retinoic acid in experimental models of cancer", *Breast Cancer Res. and Treat.* 38: 85–96 (1996).

Graziano, M. P. et al., "The amino terminal domain of the glucagon-like peptide-1 receptor is a critical determinant of subtype specificity" *Receptors Channels* 4(1): 9–17 (1996).

Guan, X. M., et al., "Determination of Structural Domains for G Protein Coupling and Ligand Binding in (3 -Adrenergic Receptor" *Mol. Pharmacol.* 48(3): 492–498 (1995).

Gudas, L. J., et al. "Cellular biology and biochemistry of the retinoids" In: Sporn, M. B., Roberts, A. B., Goodman, D. S. eds. *The retinoids: Biology, chemistry, and medicine.* $2^{nd}$ ed. New York: Raven Press. p. 443–520 (1994).

Gundersen, C. B., et al., "Serotonin receptors induced by exogenous messenger RNA in Xenopus oocytes" *Proc. R. Soc. Lond. B. Biol. Sci.* 219(1214): 103–109 (1983).

Hofman, C. and Eichele, G., "Retinoids in development" In: Sporn, M. B., Roberts, A. B., Goodman, D. S. eds. *The retinoids: Biology, chemistry. and medicine.* $2^{nd}$ ed. New York: Raven Press. p. 387–441 (1994).

Inanobe, A., et al., "Characterization of G-protein-gated K+ channels composed of Kir3.2 subunits in dopaminergic neurons of the substantia nigra" *J. of Neurosci.* 19(3): 1006–1017 (1999).

Krapivinsky, G., et al., "The G-protein-gated atrial $K^+$ channel IKACh is a heteromultimer of two inwardly rectifying K(+) -channel proteins" *Nature* 374:135–141 (1995).

Krapivinsky, G., et al., "The cardiac inward rectifier K+ channel subunit, CIR, does not comprise the ATP-sensitive K+ channel, IKATP", *J. Biol. Chem.* 270:28777–28779 (1995b).

Kubo, Y., et al., "Primary structure and functional expression of a rat G-protein-coupled muscarinic potassium channel" *Nature* 364:802–806 (1993).

Lazareno, S. and Birdsall, N. J. M., "Pharmacological characterization of acetylcholine stimulated [$^{35}$S]-GTPγS binding mediated by human muscarinic m1–m4 receptors: antagonist studies", *Br. J. Pharmacol.* 109: 1120–1127 (1993).

Manglesdorf, D. J., et al. "The retinoid receptors", In: Sporn, M. B., Roberts, A. B., Goodman, D. S. eds. *The retinoids: Biology. chemistry. and medicine.* 2$^{nd}$ ed. New York: Raven Press. p. 319–349 (1994). Martin, S., et al., "HL-60 cells induced to differentiate towards neutrophils subsequently die via apoptosis" *Clin. Exp. Immunol.* 79: 448–453 (1990).

Miller, J., and Germain, R. N. "Efficient cell surface expression of class II MHC molecules in the absence of associated invariant chain", *J. Exp. Med.* 164(5): 1478–1489 (1986).

Milligan, G., et al., "Use of chimeric G (proteins in drug discovery" *TIPS* (In press).

Ohmura, T., et al., "Induction of cellular DNA synthesis in the pancreas and kidneys of rats by peroxisome proliferators, 9-cis retinoic acid, and 3,3',5-triiodo-L-thyronine", *Cancer Res.* 57: 795–798 (1997).

Orfanos, C. E., et al., "Current use and future potential role of retinoids in dermatology", *Drugs* 53(3): 358–388 (1997).

Quick, M. W. and Lester, H. A., "Methods for expression of excitability proteins in Xenopus oocytes", *Meth. Neurosci.* 19: 261–279 (1994).

Redfern, C. P., et al., "Gene expression and neuroblastoma cell differentiation in response to retinoic acid: differential effects of 9-cis and all-trans retinoic acid" *Eur. J. Cancer* 31A(4): 486–494 (1995).

Riordan, J. R., "The cystic fibrosis transmembrane conductance regulator", *Ann. Rev. Physiol.* 55: 609–630 (1993).

Rosenwicz, S., Wollbergs, K., Von Lampe, B., Matthes, H., Kaiser, A., and E. O. Riecken (1997) Retinoids inhibit adhesion to laminin in human pancreatic carcinoma cells via the alpha 6 beta 1-integrin receptor. *Gastroenterology* 112 (2): 532–542.

Rosenwicz, S., Stier, U., Brembeck, F., Kaiser, A., Papadimitriou, C. A., Berdel, W. E., Wiedenmann, B., and E. O. Riecken (1995) Retinoids: effects on grownth, differentiation, and nuclear receptor expression in human pancreatic carcinoma cell lines. *Gastroenterology* 109(5): 1646–1660.

Sabichi, A. L., et al., "Retinoids in the chemoprevention of bladder cancer", *Curr. Opin. Oncol.* 10 (5): 479–484 (1998).

Salon, J. A. and Owicki, J. A., "Real-time measurements of receptor activity: Application of microphysiometric techniques to receptor biology" *Meth. Neurosci.* 25: 201–224 (1996).

Smith, K. E., et al., "Expression cloning of a rat hypothalamic galanin receptor coupled to phosphoinositide turnover", *J. Biol. Chem.* 272: 24612–24616 (1997).

Sporn, M., and Roberts, A., "Role of retinoids in differentiation and carcinogenesis" *J. Natl. Cancer Inst.* 73: 1381–1387(1984).

Spurney, R. F., et al., "The C-terminus of the thromboxane receptor contributes to coupling and desensitization in a mouse mesangial cell line", *J. Pharmacol. Exp. Ther.* 283 (1): 207–215 (1997).

Takahashi, T., et al., ARat brain serotonin receptors in Xenopus oocytes are coupled by intracellular calcium to endogenous channels@ *Proc. Natl. Acad. Sci. USA* 84(14) 5063–5067 (1987).

Tian, W., et al., "Determinants of alpha-Adrenergic Receptor Activation of G protein: Evidence for a Precoupled Receptor/G protein State" *Molecular Pharm.* 45: 524–553 (1994).

Underwood, D. J. et al., "Structural model of antagonist and agonist binding to the angiotensin II, AT1 subtype, G protein coupled receptor", *Chem. Biol.* 1(4): 211–221 (1994).

What is claimed is:

1. An isolated nucleic acid encoding a human or rat SNORF25 receptor, wherein the human SNORF25 receptor has an amino acid sequence identical to the amino acid sequence shown in FIGS. 2A–2B (SEQ ID NO: 2) or that encoded by plasmid pEXJT3T7-hSNORF25 (ATCC Accession No. 203495); and the rat SNORF25 receptor has an amino acid sequence identical to the amino acid sequence shown in FIGS. 4A–4B (SEQ ID NO: 4) or that encoded by plasmid pcDNA3.1-rSNORF25 (ATCC Accession No. 203494).

2. The nucleic acid of claim 1, wherein the nucleic acid is DNA.

3. The DNA of claim 2, wherein the DNA is cDNA.

4. The DNA of claim 2, wherein the DNA is genomic DNA.

5. The nucleic acid of claim 1, wherein the nucleic acid is RNA.

6. A vector comprising the nucleic acid of claim 1.

7. A vector of claim 6 adapted for expression in a cell which vector comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell.

8. The vector of claim 7, wherein the vector is a baculovirus.

9. The vector of claim 6, wherein the vector is a plasmid.

10. The plasmid of claim 9 designated pEXJT3T7-hSNORF25 (ATCC Accession No. 203495).

11. The plasmid of claim 9 designated pcDNA3.1-rSNORF25 (ATCC Accession No. 203494).

12. A cell comprising the vector of claim 9.

13. A cell of claim 12, wherein the cell is a non-mammalian cell.

14. A cell of claim 13, wherein the non-mammalian cell is a Xenopus oocyte cell or a Xenopus melanophore cell.

15. A cell of claim 12, wherein the cell is a mammalian cell.

16. A mammalian cell of claim 15, wherein the cell is a COS-7 cell, a 293 human embryonic kidney cell, a NIH-3T3 cell, a LM(tk−) cell, a mouse Y1 cell, or a CHO cell.

17. A cell of claim 12, wherein the cell is an insect cell.

18. An insect cell of claim 17, wherein the insect cell is an Sf9 cell, an Sf21 cell or a Trichoplusia ni 5B-4 cell.

19. A membrane preparation isolated from the cell of any one of claims 12, 13, 15, 16, 17 or 18, wherein the membrane preparation comprises recombinantly produced SNORF25.

20. A recombinant nucleic acid comprising a nucleic acid encoding a human SNORF25 receptor, wherein the human SNORF25 receptor comprises an amino acid sequence identical to the sequence of the human SNORF25 receptor encoded by the nucleotide sequence beginning at the start codon at positions 61–63 and ending at the stop codon at positions 1066–1068 as indicated in FIGS. 1A–1B (SEQ ID NO: 1).

21. A recombinant nucleic acid comprising a nucleic acid encoding a rat SNORF25 receptor, wherein the rat SNORF25 receptor comprises an amino acid sequence identical to the sequence of the rat SNORF25 receptor encoded by the nucleotide sequence beginning at the start codon at positions 49–51 and ending at the stop codon at positions 1054–1056 as indicated in FIGS. 3A–3B (SEQ ID NO: 3).

* * * * *

Adverse Decision in Interference

Patent No. 6,221,660, James A. Bonini, Beth E. Borowsky, Nika Adham, Noel Boyle, Thelma O. Thompson, DNA ENCODING SNORF25 RECEPTOR, Interference No. 105,542, final judgment adverse to the patentees rendered June 26, 2007, as to claims 1-3, 5-9 and 12-20.

*(Official Gazette July 29, 2008)*

SEQUENCE LISTING

```
<160> NUMBER OF SEQ ID NOS: 23

<210> SEQ ID NO 1
<211> LENGTH: 1129
<212> TYPE: DNA
<213> ORGANISM: Homo sapiens

<400> SEQUENCE: 1
tgagaatttc agctggagag atagcatgcc ctggtaagtg aagtcctgcc acttcgagac      60
atggaatcat ctttctcatt tggagtgatc cttgctgtcc tggcctccct catcattgct     120
actaacacac tagtggctgt ggctgtgctg ctgttgatcc acaagaatga tggtgtcagt     180
ctctgcttca ccttgaatct ggctgtggct gacaccttga ttggtgtggc catctctggc     240
ctactcacag accagctctc cagcccttct cggcccacac agaagaccct gtgcagcctg     300
cggatggcat ttgtcacttc ctccgcagct gcctctgtcc tcacggtcat gctgatcacc     360
```

-continued

```
tttgacaggt accttgccat caagcagccc ttccgctact tgaagatcat gagtgggttc    420
gtggccgggg cctgcattgc cgggctgtgg ttagtgtctt acctcattgg cttcctccca    480
ctcggaatcc ccatgttcca gcagactgcc tacaaagggc agtgcagctt ctttgctgta    540
tttcaccctc acttcgtgct gaccctctcc tgcgttggct tcttcccagc catgctcctc    600
tttgtcttct tctactgcga catgctcaag attgcctcca tgcacagcca gcagattcga    660
aagatggaac atgcaggagc catggctgga ggttatcgat ccccacggac tcccagcgac    720
ttcaaagctc tccgtactgt gtctgttctc attgggagct tgctctatc ctgaccccc     780 ttccttatca ctggcattgt gcaggtggcc tgccaggagt gtcacctcta cctagtgctg    840
gaacggtacc tgtggctgct cggcgtgggc aactccctgc tcaacccact catctatgcc    900
tattggcaga aggaggtgcg actgcagctc taccacatgg ccctaggagt gaagaaggtg    960
ctcacctcat tcctcctctt tctctcggcc aggaattgtg gcccagagag gcccagggaa    1020
agttcctgtc acatcgtcac tatctccagc tcagagtttg atggctaaga cggtaagggc    1080
agagaagttt caaagtgcct ttctcctccc actctggagc cccaactag              1129
```

<210> SEQ ID NO 2
<211> LENGTH: 335
<212> TYPE: PRT
<213> ORGANISM: Homo sapiens

<400> SEQUENCE: 2

```
Met Glu Ser Ser Phe Ser Phe Gly Val Ile Leu Ala Val Leu Ala Ser
 1               5                  10                  15

Leu Ile Ile Ala Thr Asn Thr Leu Val Ala Val Ala Val Leu Leu Leu
                20                  25                  30

Ile His Lys Asn Asp Gly Val Ser Leu Cys Phe Thr Leu Asn Leu Ala
            35                  40                  45

Val Ala Asp Thr Leu Ile Gly Val Ala Ile Ser Gly Leu Leu Thr Asp
        50                  55                  60

Gln Leu Ser Ser Pro Ser Arg Pro Thr Gln Lys Thr Leu Cys Ser Leu
 65                  70                  75                  80

Arg Met Ala Phe Val Thr Ser Ser Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240
```

```
Phe Leu Ile Thr Gly Ile Val Gln Val Ala Cys Gln Glu Cys His Leu
                245                 250                 255

Tyr Leu Val Leu Glu Arg Tyr Leu Trp Leu Gly Val Gly Asn Ser
        260                 265                 270

Leu Leu Asn Pro Leu Ile Tyr Ala Tyr Trp Gln Lys Glu Val Arg Leu
        275                 280                 285

Gln Leu Tyr His Met Ala Leu Gly Val Lys Lys Val Leu Thr Ser Phe
        290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
                325                 330                 335

<210> SEQ ID NO 3
<211> LENGTH: 1082
<212> TYPE: DNA
<213> ORGANISM: Rattus norvegicus

<400> SEQUENCE: 3
tcaagaccca gcatgccctt ataagtggga gtcctgctac ctcgaaccat ggagtcatct      60
ttctcatttg gagtgatcct tgctgtcctg accatcctta tcattgctgt taatgcgctg    120
gtggttgtgg ctatgctgct atcaatctac aagaatgatg gtgttggcct ttgcttcacc    180
ttaaatctgg ccgtggctga taccttgatt ggcgtggcta tttctgggct agttacagac    240
cagctctcca gctctgctca gcacacacag aagaccttgt gtagccttcg gatggcattc    300
gtcacttctt ctgcagccgc ctctgtcctc acggtcatgc tgattgcctt tgacaggtac    360
ctggccatta agcagcccct ccgttacttc agatcatga atgggcttgt agccggagga    420
tgcattgcag gctgtggtt gatatcttac cttatcggct cctcccact gggagtctcc    480 atattccagc agaccaccta ccatgggccc tgcaccttct ttgctgtgtt tcacccaagg    540
tttgtgctga ccctctcctg tgctggcttc ttcccagctg tgctcctctt tgtcttcttc    600
tactgtgaca tgctcaagat tgcctctgtg cacagccagc acatccggaa gatgaacat    660 gcaggagcca tggttggagc ttgccggccc ccacggcctg tcaatgactt caaggctgtc    720
cggactgtat ctgtccttat tgggagcttc accctgtcct ggtctccgtt tctcatcact    780
agcattgtgc aggtggcctg ccacaaatgc tgcctctacc aagtgctgga aaaatacctc    840
tggctccttg gagttggcaa ctccctgctc aacccactca tctatgccta ttggcagagg    900
gaggttcggc agcagctctg ccacatggcc ctggggggtga agaagttctt tacttcaatc    960
ttcctcctcc tctcggccag gaatcgtggt ccacagagga cccgagaaag ctcctatcac   1020
atcgtcacta tcagccagcc ggagctcgat ggctaggatg gtaaggaatg gatgtttcca   1080
ag                                                                 1082

<210> SEQ ID NO 4
<211> LENGTH: 335
<212> TYPE: PRT
<213> ORGANISM: Rattus norvegicus

<400> SEQUENCE: 4

Met Glu Ser Ser Phe Ser Phe Gly Val Ile Leu Ala Val Leu Thr Ile
  1               5                  10                  15

Leu Ile Ile Ala Val Asn Ala Leu Val Val Val Ala Met Leu Leu Ser
             20                  25                  30

Ile Tyr Lys Asn Asp Gly Val Gly Leu Cys Phe Thr Leu Asn Leu Ala
```

-continued

```
                 35                  40                  45
Val Ala Asp Thr Leu Ile Gly Val Ala Ile Ser Gly Leu Val Thr Asp
     50                  55                  60
Gln Leu Ser Ser Ser Ala Gln His Thr Gln Lys Thr Leu Cys Ser Leu
 65                  70                  75                  80
Arg Met Ala Phe Val Thr Ser Ser Ala Ala Ser Val Leu Thr Val
                 85                  90                  95
Met Leu Ile Ala Phe Asp Arg Tyr Leu Ala Ile Lys Gln Pro Leu Arg
                100                 105                 110
Tyr Phe Gln Ile Met Asn Gly Leu Val Ala Gly Gly Cys Ile Ala Gly
            115                 120                 125
Leu Trp Leu Ile Ser Tyr Leu Ile Gly Phe Leu Pro Leu Gly Val Ser
        130                 135                 140
Ile Phe Gln Gln Thr Thr Tyr His Gly Pro Cys Thr Phe Phe Ala Val
145                 150                 155                 160
Phe His Pro Arg Phe Val Leu Thr Leu Ser Cys Ala Gly Phe Pro
                165                 170                 175
Ala Val Leu Leu Phe Val Phe Tyr Cys Asp Met Leu Lys Ile Ala
            180                 185                 190
Ser Val His Ser Gln His Ile Arg Lys Met Glu His Ala Gly Ala Met
        195                 200                 205
Val Gly Ala Cys Arg Pro Pro Arg Pro Val Asn Asp Phe Lys Ala Val
210                 215                 220
Arg Thr Val Ser Val Leu Ile Gly Ser Phe Thr Leu Ser Trp Ser Pro
225                 230                 235                 240
Phe Leu Ile Thr Ser Ile Val Gln Val Ala Cys His Lys Cys Cys Leu
                245                 250                 255
Tyr Gln Val Leu Glu Lys Tyr Leu Trp Leu Leu Gly Val Gly Asn Ser
            260                 265                 270
Leu Leu Asn Pro Leu Ile Tyr Ala Tyr Trp Gln Arg Glu Val Arg Gln
        275                 280                 285
Gln Leu Cys His Met Ala Leu Gly Val Lys Lys Phe Phe Thr Ser Ile
    290                 295                 300
Phe Leu Leu Leu Ser Ala Arg Asn Arg Gly Pro Gln Arg Thr Arg Glu
305                 310                 315                 320
Ser Ser Tyr His Ile Val Thr Ile Ser Gln Pro Glu Leu Asp Gly
                325                 330                 335
```

<210> SEQ ID NO 5
<211> LENGTH: 21
<212> TYPE: DNA
<213> ORGANISM: Artificial Sequence
<220> FEATURE:
<223> OTHER INFORMATION: n = inosine
<220> FEATURE:
<223> OTHER INFORMATION: Description of Artificial Sequence:
      primer/probe

<400> SEQUENCE: 5
tbdsyvynga ymgntayvtk g 21

<210> SEQ ID NO 6
<211> LENGTH: 26
<212> TYPE: DNA
<213> ORGANISM: Artificial Sequence
<220> FEATURE:
<223> OTHER INFORMATION: n = inosine
<220> FEATURE:

<223> OTHER INFORMATION: Description of Artificial Sequence:
      primer/probe

<400> SEQUENCE: 6
ganrsnarng mrtanaynak nggrtt                                      26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 7
ttatgcttcc ggctcgtatg ttgtg                                       25

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      primer/probe

<400> SEQUENCE: 8
atgtgctgca aggcgattta agttggg                                     27

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 9
tggtctgctg gaatatggag                                             20

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      primer/probe

<400> SEQUENCE: 10
cttgggtgaa acacagcaaa gaagg                                       25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
atggaacatg caggagccat ggttgg                                      26

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:

primer/probe

<400> SEQUENCE: 12
aagacaaaga ggagcacagc tggg                                           24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 13
gctcaagatt gcctctgtgc acag                                           24

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      primer/probe

<400> SEQUENCE: 14
atctataagc ttaggcactt ggaaacatcc attcc                               35

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:
      primer/probe

<400> SEQUENCE: 15
atctatggat cctgtgagaa tctgagctca agaccc                              36

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence:
      primer/probe

<400> SEQUENCE: 16
ttcaccttaa atctggccgt ggctgatacc ttgattggcg tggctatttc tgggctag      58

<210> SEQ ID NO 17
<211> LENGTH: 61
<212> TYPE: DNA
<213> ORGANISM: Artificial Sequence
<220> FEATURE:
<223> OTHER INFORMATION: Description of Artificial Sequence:
      primer/probe

<400> SEQUENCE: 17
gctgtgtttc acccaaggtt tgtgctgacc ctctcctgtg ctggcttctt cccagctgtg    60
c                                                                    61

<210> SEQ ID NO 18
<211> LENGTH: 22
<212> TYPE: DNA
<213> ORGANISM: Artificial Sequence
<220> FEATURE:

-continued

```
<223> OTHER INFORMATION: Description of Artificial Sequence:
      primer/probe

<400> SEQUENCE: 18
cctctaccta gtgctggaac gg                                                  22

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 19
gctgcagtcg cacctcct                                                       18

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:
      primer/probe

<400> SEQUENCE: 20
tccctgctca acccactcat ctatgcctat t                                        31

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:
      primer/probe

<400> SEQUENCE: 21
gtgtagcctt cggatggca                                                      19

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      primer/probe

<400> SEQUENCE: 22
ggctgcttaa tggccaggta c                                                   21

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence:
      primer/probe

<400> SEQUENCE: 23
tcctcacggt catgctgatt gcctttt                                             26
```